United States Patent
Usui et al.

(10) Patent No.: US 7,611,767 B2
(45) Date of Patent: Nov. 3, 2009

(54) FOOT WARMING HEATING ELEMENT AND METHOD OF MANUFACTURING FOOT WARMING HEATING ELEMENT

(75) Inventors: Kaoru Usui, Tochigi (JP); Michio Aida, Tochigi (JP); Hisao Kimura, Tochigi (JP); Masato Nakamura, Tochigi (JP); Yoshikazu Sakamaki, Tochigi (JP); Toshihiro Dodo, Tochigi (JP)

(73) Assignee: Mycoal Co., Ltd., Tochigi-shi (JP)

( * ) Notice: Subject to any disclaimer, the term of this patent is extended or adjusted under 35 U.S.C. 154(b) by 0 days.

(21) Appl. No.: 10/475,513

(22) PCT Filed: Apr. 11, 2003

(86) PCT No.: PCT/JP03/04653

§ 371 (c)(1),
(2), (4) Date: Oct. 27, 2003

(87) PCT Pub. No.: WO03/096942

PCT Pub. Date: Nov. 27, 2003

(65) Prior Publication Data

US 2004/0149732 A1    Aug. 5, 2004

(30) Foreign Application Priority Data

May 20, 2002    (JP) ............................ 2002-183685

(51) Int. Cl.
*B32B 5/22* (2006.01)
*B32B 37/00* (2006.01)
(52) U.S. Cl. ................. 428/208; 428/195.1; 428/206; 428/320.2; 428/343; 428/354; 126/263.01; 126/263.02; 156/145; 156/250
(58) Field of Classification Search ................. None
See application file for complete search history.

(56) References Cited

U.S. PATENT DOCUMENTS

| 5,046,479 | A | 9/1991 | Usui |
| 5,084,986 | A | 2/1992 | Usui |
| 5,879,378 | A | 3/1999 | Usui |
| 6,264,681 | B1 * | 7/2001 | Usui .................... 607/111 |
| 6,436,128 | B1 | 8/2002 | Usui |

(Continued)

OTHER PUBLICATIONS

U.S. Appl. No. 10/450,521, filed Jun. 19, 2003, Usui et al.

*Primary Examiner*—Monique R Jackson
(74) *Attorney, Agent, or Firm*—Edwards Angell Palmer & Dodge LLP

(57) ABSTRACT

There is provided such a heat-generating body for warming a foot in that a heat-generating composition is used that can retain the shape thereof irrespective of the pressure inside the container bag upon using by application to a foot, a footgear or a sock. The heat-generating body of the invention for warming a foot is characterized in that it contains a heat-generating formed article causing a heat-generating reaction in the presence of air and having a shape retaining degree of 70 or more charged in a container bag constituted with a base material, a covering material and the like. Further a process is provided for producing a heat-generating body for warming a foot in that the heat generation reaction of the heat-generating composition is suppressed to prevent loss due to the heat-generating reaction during production, quality deterioration of the heat-generating composition, and other problems.

18 Claims, 9 Drawing Sheets

U.S. PATENT DOCUMENTS

| | | | |
|---|---|---|---|
| 6,915,798 B2 * | 7/2005 | Minami | 126/263.02 |
| 2001/0023366 A1 | 9/2001 | Usui | |
| 2002/0121624 A1 | 9/2002 | Usui | |
| 2004/0149732 A1 | 8/2004 | Usui et al. | |

* cited by examiner

Before Test

After Test

Composition

FOOT WARMING HEATING ELEMENT AND METHOD OF MANUFACTURING FOOT WARMING HEATING ELEMENT

TECHNICAL FIELD

The present invention relates to a heat-generating body for foot supplying heat to foot, and in particular, to such a heat-generating body for warming foot in that, particularly upon using by attaching to foot, shoes or socks, it has various kinds of shapes of from an ultrathin shape to a thick shape and can maintain the shape of a heat-generating composition irrespective of the pressure inside a container bag, whereby a part or the whole of the heat-generating composition can be fixed in a packing material and can be prevented from migration, and moreover, it is well fitted to the shape of foot upon attaching thereto, and can reach the prescribed temperature in a short period of time to warm the objective part effectively for a long period of time, and the invention also relates to such a process for producing a heat-generating body for foot that can produce a heat-generating body for foot having various shapes of from an ultrathin shape to a thick shape in a simple manner at a low cost.

BACKGROUND ART

It has been conventionally proposed that a heat-generating body utilizing a heat-generating composition containing metallic powder, such as iron powder, as a major component in a powder form, a paste form or the like and utilizing reaction heat with oxygen in air is applied to a footwear, such as shoes, slippers, to warm foot.

For example, it has been proposed that a housing part of the heat-generating body is formed in a sole insert of a shoe, and a heat-generating body charged in an air permeable bag is provided inside the housing part (JP-A-U-S61-8013).

Such a heat-generating body for keeping heat in a shoe has also been proposed that has a heat-generating body in a shoe sole form having black kraft paper attached on an inside thereof (JP-A-U-H3-7706).

Furthermore, such a heat-generating body for foot such as for a shoe has been proposed in that a heat-generating agent is charged in a flat air permeable bag body having a shape adapted for a partial shape of foot, and a non-transferable adhesive agent layer is provided on one surface of the air permeable bag body, whereby it is adhered to the surface of foot with the non-transferable cohesive agent layer (JP-A-H2-172460).

A method for fixing a heat-generating composition with a cohesive agent is proposed in JP-A-S62-347, but it is substantially impossible to adhere a powder heat-generating composition on an inside of a bag body in practical productions, and even if it is possible, it lacks in practicability because the adhesion strength is small to fail to attain complete fixing, which causes releasing during the use, the use feeling is deteriorated due to a platy shape having poor flexibility, and in addition, contact with air is considerably impaired due to the presence of the mixed adhesives to cause nonuniformity and fluctuation in temperature.

Other proposals of heat-generating bodies for warming foot have been made, for example, in JP-A-H2-154762, JP-A-H5-115310, JP-A-U-H6-21616, JP-A-U-H5-84317 and JP-A-H5-176951.

Such a process has been generally employed as a process for producing the heat-generating body for warming foot in that after dropping a powder heat-generating composition containing water on a prescribed region of a base material, a covering material having air permeability is overlaid thereon, and thereafter, a peripheral part of the base material and the covering material is sealed wholly by heat sealing, a hot-melt adhesive or the like.

In alternative, such a process is employed in that a heat-generating composition in a viscous cream form is laminated on a base material in a film or sheet form by printing, which is covered with a covering material, and a peripheral part of the base material and the covering material is sealed wholly by heat sealing, a hot-melt adhesive or the like.

Examples of the conventional heat-generating body for warming foot include the one formed by mixing, in addition to metallic powder, such as iron powder, and water, activated carbon for accelerating heat generation, a metallic chloride for continuously inducing a heat-generating reaction by breaking an oxide film on the surface of the metallic powder, a water absorbing agent for preventing tackiness, and the like in conventionally suitable proportions, and the heat-generating composition is in a powder form containing water and is dropped on a base material.

Examples of the method for dropping the powder heat-generating composition include a method of moving the base material intermittently and dropping the heat-generating composition during suspension of the base material, and a method of moving the base material at a constant velocity, and dropping the heat-generating composition on the base material while moving the dropping mesh for dropping the heat-generating composition at the same velocity as the base material.

Furthermore, a production using a lamination method and the like by printing, such as screen printing, coating and the like is also employed for a paste heat-generating composition formed into a viscous heat-generating composition by adding viscosity to the heat-generating composition by containing a thickener (JP-A-H9-276317).

A heat-generating body for warming foot having a prolonged heating duration is difficult to produce at a high speed, and migration of the heat-generating composition inside the container bag occurs upon use to deform the heat-generating body itself, and thus the use feeling is considerably deteriorated. On the other hand, such a heat-generating body for warming foot that can be produced at a high speed, in which the heat-generating composition does not move inside the container bag during use to prevent the heat-generating body itself from deformation has a short heating duration and has problems as a practical product.

There has been no heat-generating body for warming foot with good use feeling that can be produced at a high speed, has a prolonged heating duration, is free of migration of the heat-generating composition inside the container bag upon use to prevent the heat-generating composition itself from deformation.

That is, in a heat-generating body for warming foot having a conventional powder heat-generating composition, the heat-generating body for warming foot is bulky in total and is poor in texture with stiff feeling. Furthermore, it is poor in flexibility and is difficult to fit complex unevenness and curved surfaces with small curvature on the surface of a human body. Moreover, since the elongation property or the stretch property is lowered, the heat-generating composition moves associated with movement of the human body, and the heat-generating body is deformed, whereby the followability of the heat-generating body to the surface is deteriorated to cause such a problem that the use feeling is considerably deteriorated.

The heat-generating body having a conventional powder heat-generating composition can follow only a rough curved surface and partially causes warpage due to misfit in curved surfaces depending on the kind of shoes, so as to cause pain on foot by pressing foot, whereby the applicable shoes are restricted to provide significant unsatisfaction.

In the heat-generating body having a conventional powder heat-generating composition, although the heat-generating composition is imparted with wettability with water, the mixing ratio of water is as low as such an extent that is suitable for the heat-generating reaction, and it is in the form of powder and is poor in flowability. Therefore, it is considerably difficult to be uniformly distributed within the prescribed region on the base material, and thus the thickness of the heat-generating composition is fluctuated inside the heat-generating body for warming foot, whereby the heat-generating composition moves inside the inner bag, or the heat-generating composition is deviated due to deviation and bending thereof, so that the thickness of the heat-generating composition inside the heat-generating body for warming foot becomes unequable. Accordingly, in the case where it is used by fixing on a human body, it causes such serious problems in that there are cases where ambustion occurs due to the unevenness in heat generation temperature distribution upon using by fixing on the same position, the skin receives a powerful stimulus, dermopathy, such as rubefaction, eruption, skin fit, arises.

In the method for fixing a powder heat-generating composition with an cohesive, it is substantially impossible upon practical production that the powder heat-generating composition is adhered on the inside surface of the bag material, and even when it is possible, the adhesion strength is small to fail to attain complete fixation, but it is released during use, and only a plate-like material with poor flexibility is obtained to impair practicality by deteriorating use feeling and by causing unevenness and fluctuation in temperature.

On the other hand, a heat-generating composition using a thickener having a viscous paste or cream form is good in moldability to retain uniformity in thickness, but is restricted in practicality because drainage of excessive water is insufficient, and desired heat generation amount and heat generation duration cannot be obtained due to influences of the thickener and a binder to fail to produce a large size product and to fail to obtain a prolonged heat-generating duration.

In the case of the viscous heat-generating composition in a paste or cream form, if the adhesiveness to a base material is poor, a laminated material is peeled from the base material upon molding by pulling by an unlaminated heat-generating composition due to cohesiveness of the heat-generating composition, so as to cause unevenness in thickness, and there are some cases where a normal sole shape cannot be obtained to restrict the base material.

In the conventional powder heat-generating composition or the conventional semi-kneaded heat-generating composition, because water is mixed only in such an amount that is suitable for the heat-generating reaction, the heat-generating reaction smoothly and continuously proceeds immediately upon contacting with air. As a result, the heat-generating reaction occurs after mixing the heat-generating composition but before charging the heat-generating body thus produced in an outer bag, and the vapor pressure of water in the heat-generating composition is increased to expand the heat-generating body, so as to cause such a problem in that the expanded heat-generating body is difficult to be charged in a packing bag having air nonpermeability.

Furthermore, in the conventional heat-generating composition, a heat-generating reaction occurs after mixing the heat-generating composition but before charging the heat-generating body thus produced in an outer bag to cause loss due to the heat-generating reaction and to deteriorate the quality of the heat-generating composition, and furthermore, the reaction product formed by the heat-generating reaction is solidified causes various problems, such as reduction in yield, difficulty in handling, complication in maintenance of a production apparatus, restrictions in operation time of a production apparatus and in working time of an operator, difficulty in processing the solidified matter, and the like problems.

In the method of intermittently moving a base material and dropping a heat-generating composition during suspension of the base material, there is a problem that the production rate is lowered due to the frequent repetition of suspension and start-up of the base material.

In the method of moving a base material at a constant velocity and dropping the heat-generating composition on the base material while moving the dropping mesh for dropping the heat-generating composition at the same velocity as the base material, although the production rate can be increased since substantially no repetition of suspension and start-up of the base material occurs, a complicated mechanism is necessary for moving the dropping mesh for dropping the heat-generating composition at the same velocity as the base material, and moreover, there is a problem that the velocity of moving the mechanism is greatly restricted because the heat-generating composition contains powder and water and is poor in flowability.

Although the conventional powder heat-generating composition is imparted with wettability with water, the mixing ratio of water is as low as such an extent that is suitable for the heat-generating reaction, and it is extremely poor in flowability, whereby it is significantly difficult that the composition is uniformly distributed within the prescribed region on the base material only by simply dropping thereon.

Therefore, the distribution of the heat-generating composition is uniformized to a certain extent with a roller upon sealing with a covering material overlaid, but there is such a tendency that the distribution of the heat-generating composition is deviated to the origination side of conveying the bag material owing to the nature of the powder heat-generating composition.

The semi-kneaded heat-generating composition is such a heat-generating composition that is formed by mixing all the components including a binder at suitable proportions, and it is necessarily subjected to a tableting step, so as to complicate the process.

A heat-generating composition in a slurry form with less viscosity cannot maintain the shape to fail to attain molding into a constant shape, and it is then molded through a complicated step, such as paper making.

There are demanded a heat-generating composition having moldability, shape maintenance property, and heat generation characteristics enabling a prolonged heat generation time at the same time, a heat-generating body using the same, and a simple production process therefor.

DISCLOSURE OF THE INVENTION

The heat-generating body for warming a foot of the invention comprises a heat-generating formed article causing a heat-generating reaction in the presence of air and having a shape retaining degree of 70 or more charged in a container bag constituted with a base material, a covering material and the like, and the container bag having air permeability at least at a part thereof.

The heat-generating body for warming a foot is further characterized in that the heat-generating formed article has a water mobility value of from 3 to 50 and an incremental degree of viscosity of less than 1,000 cP and is formed by forming a non-viscous heat-generating composition having excessive water.

The heat-generating body for warming a foot is further characterized in that the non-viscous heat-generating composition is a heat-generating composition having excessive water containing, as essential components, a heat-generating substance generating heat upon reaction with oxygen, a carbon component, a reaction accelerator and water, to which at least one kind selected from a water retaining agent, a water absorbing polymer, a pH adjusting agent, a hydrogen generation suppressing agent, a syneresis preventing stabilizer, a surface active agent, a defoaming agent, a hydrophobic polymer compound, a pyroelectric substance, a far infrared ray radiating substance, a negative ion generating substance, an aggregate, a fibrous material, a thickener, a binder, a fertilizer component and a heat-generating assistant is mixed depending on necessity.

The heat-generating body for warming a foot is further characterized in that the heat-generating formed article has a structure containing two or more layers having different compositional ratios.

The heat-generating body for warming a foot is further characterized in that a part of at least one of the base material and the covering material has a water absorbing capability, water of the heat-generating formed article is absorbed by a material having water absorption property among the base material and the covering material, and it is substantially in a state capable of generating heat in air.

The heat-generating body for warming a foot is further characterized in that the container bag constituting the heat-generating body for warming foot is water nonabsorbing, and the heat-generating formed article is in a state dehydrated to enable substantial heat generation in air by at least one means selected from physical forced drainage by compression, decompression, compression and decompression, and the like, diffusion of water content by allowing to stand, and water absorption with a water absorbing material, a water absorbing agent or the like.

The heat-generating body for warming a foot is further characterized in that concave and convex parts are provided on a part of at least one of the base material and the covering material, and a heat-generating composition is provided at least on the concave part.

The heat-generating body for warming a foot is further characterized in that concave and convex parts are provided on a part of at least one of the base material, the covering material and a heat-generating composition.

The heat-generating body for warming a foot is further characterized in that an air permeable adhesive layer is provided between at least two kinds selected from the base material, the covering material and the heat-generating formed article.

The heat-generating body for warming a foot is further characterized in that the base material and the covering material are sealed at least at an outer peripheral part of the heat-generating formed article by adhesion, cohesion or fusion.

The heat-generating body for warming a foot is further characterized in that the heat-generating body for warming foot corresponds to a plane surface of an entire foot.

The heat-generating body for warming a foot is further characterized in that the heat-generating body for warming foot corresponds to a plane surface of a part of a foot.

The heat-generating body for warming a foot is further characterized in that the heat-generating body for warming foot has a part having no heat-generating formed article present, and has at least one part, at which the heat-generating body is capable of being folded up at that part.

The heat-generating body for warming a foot is further characterized in that the container bag has an antislipping function on at least a part thereof.

The heat-generating body for warming a foot is further characterized in that a adhesive agent layer is laminated on at least a part of at least one of exposed surfaces of at least one of the base material and the covering material.

The heat-generating body for warming a foot is further characterized in that a medical or sanitary agent is carried on at least one kind selected from the heat-generating formed article, an adhesive agent layer, the base material and the covering material.

The heat-generating body for warming a foot is further characterized in that at least one of a character, a symbol, a numeral, a pattern, a photograph and a picture is provided on at least a part of constitutional components of the heat-generating body for warming foot other than the heat-generating formed article.

The heat-generating body for warming a foot is further characterized in that at least a part of constitutional components of the heat-generating body for warming foot other than the heat-generating formed article is colored.

The heat-generating body for warming a foot is further characterized in that the heat-generating body for warming foot is charged and sealed in an air nonpermeable container bag.

The process for producing a heat-generating body for warming a foot is characterized in that a process for producing a heat-generating body for warming foot contains steps of laminating a heat-generating composition as described above as a heat-generating formed article laminated to a form covering an arbitrary part of a foot on at least one prescribed region on a base material in a film form or a sheet form, and overlaying a covering material, and the production process contains a step 1, a step 2 and a step 4 sequentially carried out as a basic process, and depending on necessity, with a step selected from the step 1, the step 2, a step 2A, a step 2B, a step 3, a step 3A, a step 3B, a step 3C, the step 4, a step 5, a step 6, a step 7 and a step 8 with possible duplications being subjected to arbitrary inter position in the basic process.

Step 1: a step of producing the heat-generating composition

Step 2: a step of forming

Step 2A: a forming step using a leveling plate and a magnet

Step 2B: a forming step using a pressing plate equipped with a vibrating device

Step 3: a laminating, diffusing or coating step on the heat-generating composition or the like Step 3A: a step of providing an air permeable adhesive polymer Step 3B: a laminating, diffusing or coating step on the base material or the like Step 3C: a step of subjecting the heat-generating composition to a surface treatment Step 4: a step of covering Step 4A: a step of laminating (heat fusion, press adhesion, heat press adhesion or the like)

Step 5: a step of compressing

Step 6: a step of dehydrating

Step 7: a step of punching

Step 8: a step of charging the heat-generating body in an air nonpermeable container bag

BEST MODE FOR CARRYING OUT THE INVENTION

Figure 1:
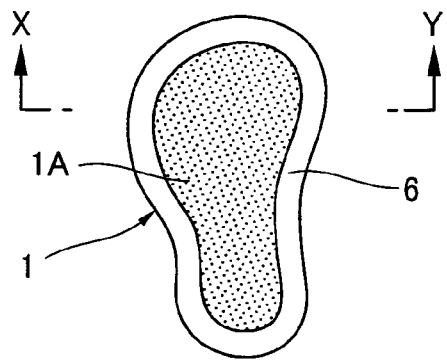
FIG. 1 is a plane view of an example of a heat-generating body of the invention.

The heat-generating body for warming foot of the invention is not restricted in shape. Specifically, it may be formed into an arbitrary shape, for example, it is formed to correspond to a plane surface of an entire foot or is formed to correspond to a plane surface of a part of a foot, such as formed to correspond to a planar shape of a top part of a foot, formed to correspond to a plane surface of a an arch of a foot, formed to correspond to a plane surface of an extended part of an arch of a foot, formed to correspond to a plane surface of a heel, and the like.

The shape of the prescribed region, on which the heat-generating composition of the invention is laminated, may be formed into such a shape that covers an arbitrary part of a foot, and examples thereof include a shape covering a part of a bottom of a foot, a shape covering a whole of a bottom of a foot, a shape covering a part of an in step of a foot, a shape covering a whole of an in step of a foot, a shape covering a part or a whole of a bottom or in step of a foot and a part or a whole of a side of a foot, a shape covering a part or a whole of a bottom of a foot, a part or a whole of a side of a foot, and a part or a whole of an in step of a foot, and the like.

Representative example of the part of a bottom of a foot include a digit, a root of a digit, a pad, an arch, a heel and the like, and examples of the shape of the heat-generating body for warming foot covering a bottom of a digit include a semicircular shape and a semiellipsoidal shape. Examples of the shape of the base material and the covering material covering a root of a digit, a pad, an arch, a heel and the like include a rectangular shape, a square shape, a trapezoidal shape, a stretched circular shape, an ellipsoidal shape, a circular shape, a semiellipsoidal shape, a semicircular shape, a horseshoe shape and the like.

Examples of the shape covering a whole of a bottom of a foot include an insole shape having the same shape as an insole of a shoe, and also include such a shape that is formed by providing a protruded part corresponding to an arch extending from a constricted part corresponding to an arch on the insole shape.

In this case, because it can be interpreted that the arch has a certain height as viewed from the side, it can also be interpreted as such a shape that covers a bottom of a foot, particularly a whole of an arch on the bottom of a foot, and a part of a side of a foot, as described next.

Examples of the shape covering a part or a whole of a bottom of a foot and a part of a side of a foot include a shape covering a whole of a bottom of a foot and a back part of an ankle extending from the bottom of a foot toward an ankle region. In this case, it can be formed by providing an insole shape covering a whole of a bottom of a foot, which is continued to a protruded part covering a back part of an ankle from the insole shape to a heel side toward an ankle region. Corresponding to a bulge of a heel, the base material and the covering material easily deform to fit the bulge of a heel.

In the case where the base material and the covering material have elongation property or stretch property, the base material and the covering material deform to fit complicated concave and convex shapes of a foot, for example, the base material and the covering material deform to fit a bulge of a heel by partially elongating as corresponding to the bulge of a heel, whereby the fitness can be further improved.

Examples of the shape covering a part or a whole of a bottom of a foot, a part or a whole of a side of a foot, and a part of an in step include a shape covering from a whole of a bottom of a foot or a bottom of digits of a foot around a toe toward an in step side of the digits of a foot, a shape of a digitated sock or a sock, and the like.

Examples of the shape covering from a whole of a bottom of a foot or a bottom of digits of a foot around a toe toward an in step side of the digits of a foot include a shape formed by providing an insole shape covering a whole of a bottom of a foot connected with a protruded part covering a toe and an in step side of digits of a foot. In this case, the size of concave and convex parts of the digits varies, and the protruded part is elongated corresponding to the concave and convex parts of the digits to have a complicated concave and convex shape covering the digits and the toe to fit ends of the digits.

Examples of the shape of a digitated sock or a sock include a shape formed in such a manner that a shape of a sock continued at a center of a sole and symmetrically divided from side by side, and after lamination, they are folded up at the center of the sole, with an edge extending from a toe through an in step to an ankle region being connected to an edge extending from a heel to the ankle region, and a shape formed in such a manner that a part of shape of a sock from an ankle region to a toe is divided from side by side to connect at a center of a bottom and to form continuously at a center of a back end thereof a protruded part covering from a heel to a back side of the ankle region, and after lamination, both side edges of the protruded part are connected to a back edge of the part from the ankle region to the toe, and both side edges of the part from the ankle region to the toe are connected to each other, and the like shapes.

According to a heat-generating body for warming foot of the invention having a continued bulge part corresponding to an arch, because it is formed by laminating a heat-generating composition in a thin film form between a base material and a covering material that have flexibility, the body has a thin form in total, and the bulge part can be easily deformed corresponding to a concave part of the arch, whereby the entire bottom of a foot can be effectively warmed with good fitness to the concave part of the arch.

Examples of an application of the heat-generating body for warming foot include a heat-generating body for warming foot that is directly applied to a foot, a heat-generating body for warming foot that is directly applied to a footgear, and a heat-generating body for warming foot for supplying heat to a foot by applying from the outside of a sock, and in the case where the footgear is a closed footgear, it is a heat-generating body for warming foot for leather shoes, rubber shoes, cloth shoes, canvas shoes, chemical shoes or sabot.

Since the heat-generating body for warming foot of the invention is formed by laminating a non-viscous heat-generating composition having excessive water on an upper surface of a base material by mold-through forming, coating or the like as described in the foregoing, the non-viscous heat-generating composition having excessive water can be uniformly laminated in a thin film form. However, it is possible that the layer thickness of the non-viscous heat-generating composition having excessive water is partly increased, so as to form to obtain an effect like acupressure in addition to the heating effect.

That is, it is possible to form a partly thick part by further laminating at least once the non-viscous heat-generating composition having excessive water on a part of the upper surface of the non-viscous heat-generating composition having excessive water having been laminated on the upper surface of the base material, or in alternative, it is also possible to thicken a part of the heat-generating composition by transferring or diffusing at least metallic powder selected from metallic powder, a water absorbing agent and a carbon component on a part of the upper surface of the non-viscous heat-generating composition having excessive water having been laminated on the upper surface of the base material.

In the case where a part of the non-viscous heat-generating composition having excessive water is thickened in these manners, the distribution of the heat generation amount can be controlled, and thus, the non-viscous heat-generating composition having excessive water can be thickened at a part such as a toe nail tip that is liable to be chill to enhance the warming effect, or in alternative, at least metallic powder selected from metallic powder, a water absorbing agent and a carbon component is transferred or diffused to absorb water forming a barrier layer, whereby the rising of the initial temperature of the heat-generating body for warming foot after taking out of an airtight outer bag can be accelerated.

In this case, it is possible that the layer thickness of the non-viscous heat-generating composition having excessive water having been laminated on the upper surface of the base material is formed to be thick at spots corresponding to an acupuncture point of a foot and/or a vicinity thereof, so as to enhance a hot moxibustion and acupressure effect.

It is of course that the number of the part where the non-viscous heat-generating composition having excessive water is thickened is not limited to only one part, but the non-viscous heat-generating composition having excessive water may be thickened at two or more plural parts.

In general, supply of air to a heat-generating body for foot is deteriorated in connection with the use condition and the application position. Therefore, it is desired upon designing a heat-generating body for warming foot that the average pore size is made relatively large as far as the heat-generating composition is not leaked, so as to improve supply of air.

The shape retaining degree is calculated by testing for one independent heat-generating body sealed on the full circumference of the heat-generating composition. In the case where there is a plurality thereof, an arithmetic average of the shape retaining degrees of the respective independent heat-generating bodies is employed.

Explanation will be made with reference to FIG. 20. A heat-generating body 1 to be measured is placed on a level place, and after confirming that a heat-generating composition is uniformly present in a heat-generating part, the maximum length S of the heat-generating part is measured. In the case where there is nonuniformity, it is uniformized.

Figure 20:
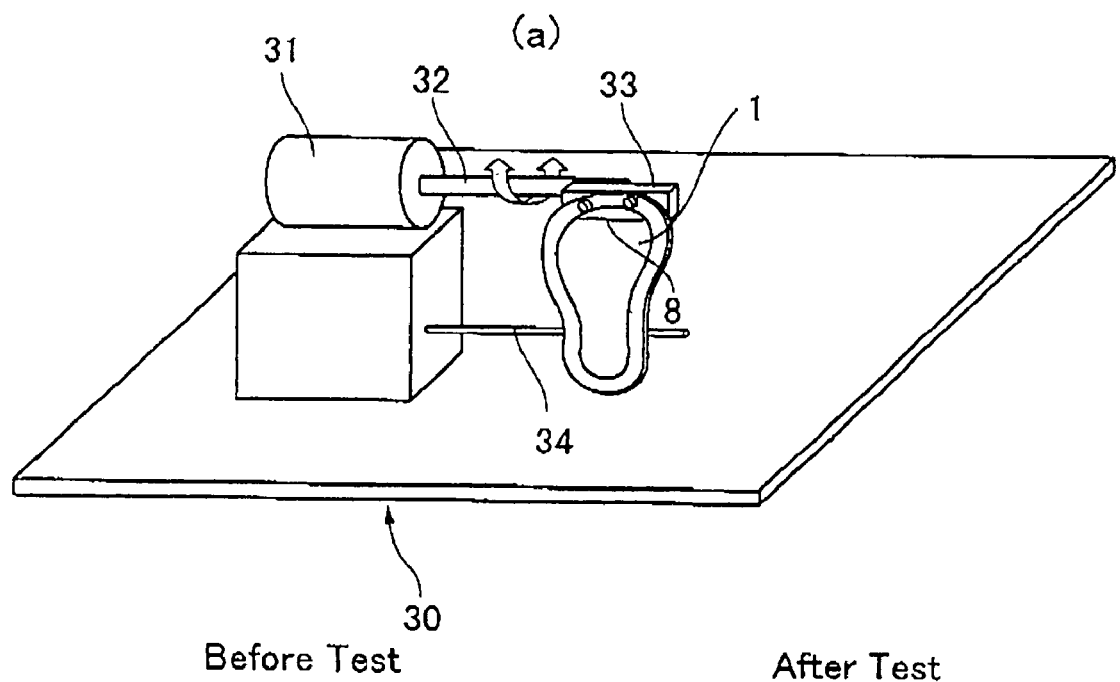
FIG. 20 is an explanatory view showing a measurement method for a shape retaining degree in the invention.
Figure 20:
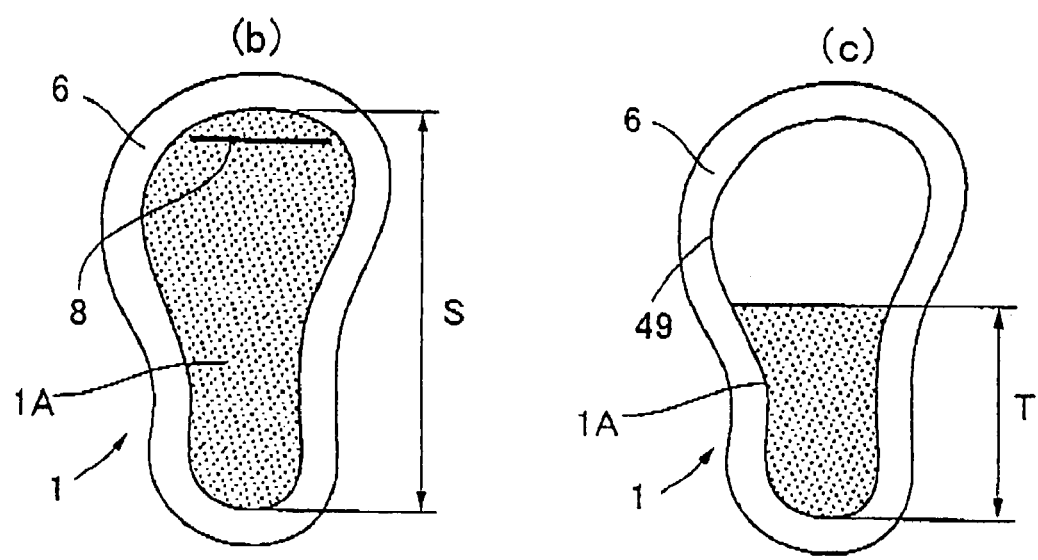

Subsequently, as shown in FIG. 20($a$), the heat-generating body 1 is fixed on a fixing plate 33 fixed on a rotation axis 32 that is rotatable with a driving source 31 of a testing machine 30. The fixed position is an upper tip end of a covering material 6 of the heat-generating body 1 where no heat-generating composition is present. A slit 8 having a length of 10 mm is made on an air permeable surface of the covering material 6 at a position of 5 mm lower from the upper end of the heat-generating part, so that the heat-generating composition 2 is under the same pressure as the outer atmospheric pressure (See FIG. 20($b$)). Thereafter, the fixing plate 33 is reciprocated by one reciprocation per second at a movement angle of 60° with rotation of the rotation axis 32, whereby the heat-generating body 1 is subjected to pendulum motion according thereto. At this time, it is made in such a way that at least a part of the heat-generating part runs on a sample beating member 34. After 10 reciprocations, the maximum length T in vertical direction of the heat-generating composition in the region of the heat-generating part occupied by the heat-generating composition with the body being fixed on the fixing plage 33 is measured (FIG. 20($c$)).

The shape retaining degree (K) herein is defined as follows.
In the case of the heat-generating body with one independent heat-generating body $$K=100 \times T/S$$

K: shaped retaining degree
S: maximum length of heat-generating composition on heat-generating part in horizontal direction before forming slit
T: maximum length of heat-generating composition on heat-generating part in vertical direction after testing
In the case of the heat-generating body with plural independent heat-generating bodies $$Km=(K1+K2+\ldots+Kn)/n$$

Kn: shape retaining degrees of respective independent heat-generating bodies obtained by equation (1)

The shape retaining degree K is generally 70 or more, preferably 80 or more, and more preferably 90 or more.

In the case where the heat-generating body is constituted from plural independent heat-generating bodies, heat-generating compositions contained in all the independent heat-generating bodies constituting the heat-generating body are measured, and the number average value of the shape retaining degrees of the respective heat-generating bodies is generally 70 or more, preferably 80 or more, and more preferably 90 or more.

In the non-viscous heat-generating composition having excessive water of the invention, the term "having excessive water" means that the water mobility value is from 3 to 50, and the term "non-viscous" means that the incremental degree of viscosity is less than 1,000 cP.

Figure 21:
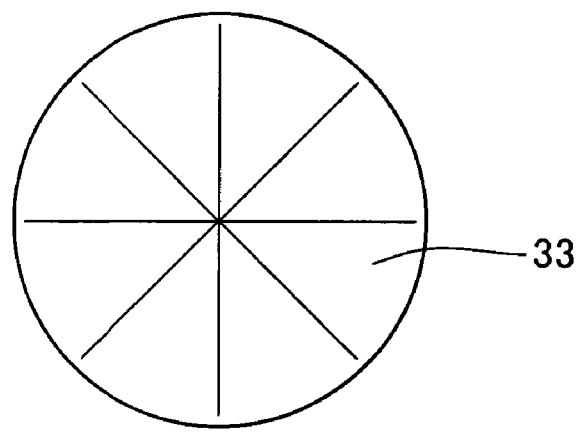
FIG. 21 is an explanatory view showing a measurement method for a water mobility value in the invention.
Figure 22:
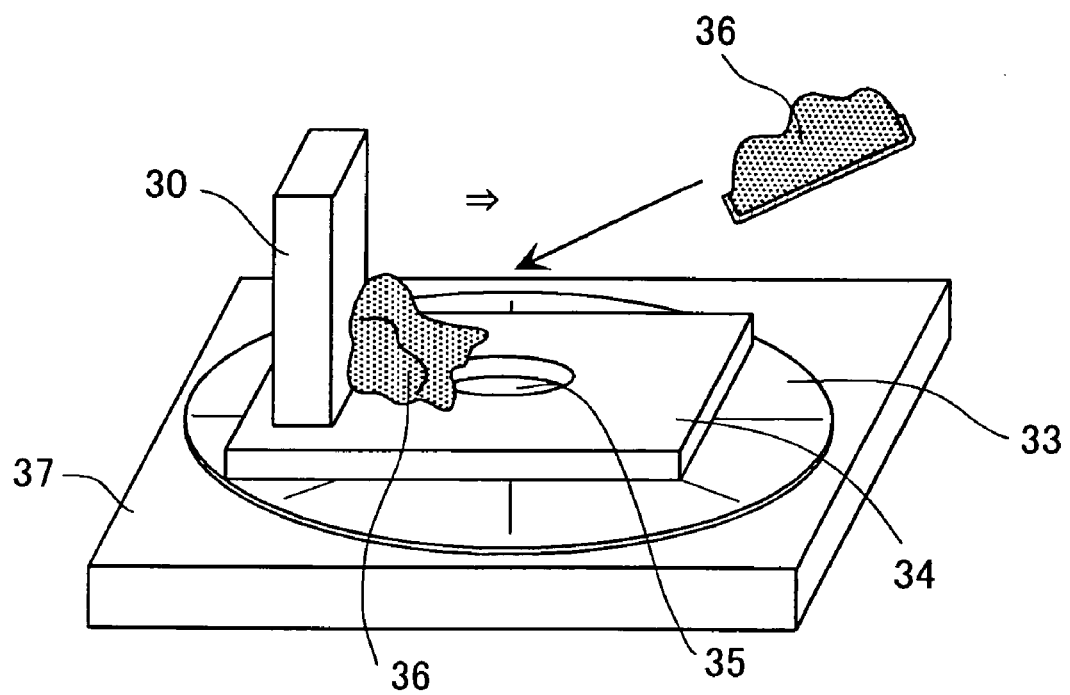
FIG. 22 is an explanatory view showing a measurement method for a water mobility value in the invention.
Figure 23:
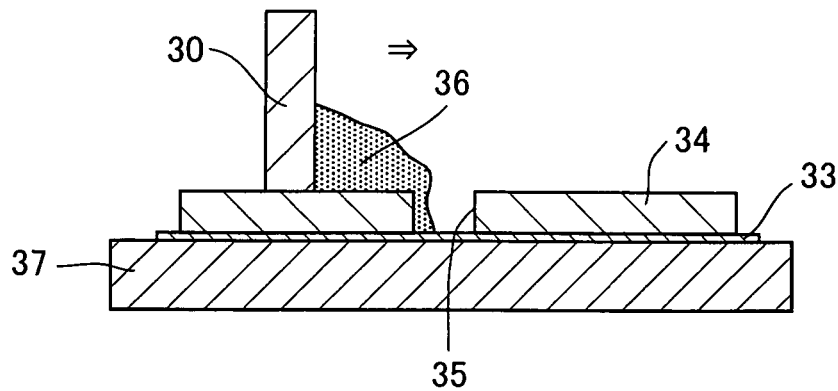
FIG. 23 is an explanatory view showing a measurement method for a water mobility value in the invention.
Figure 24:
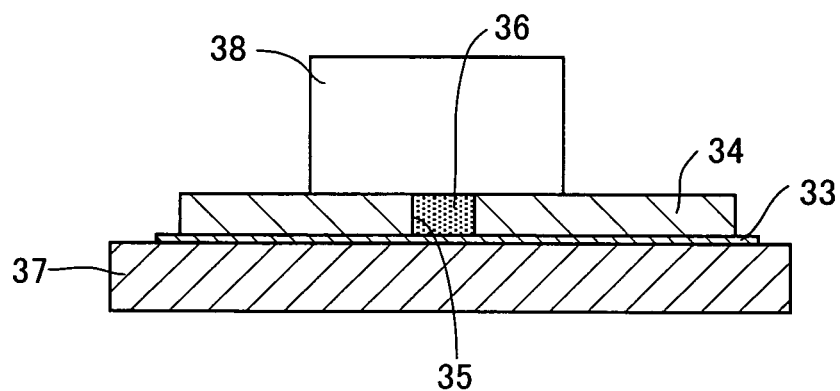
FIG. 24 is an explanatory view showing a measurement method for a water mobility value in the invention.
Figure 25:
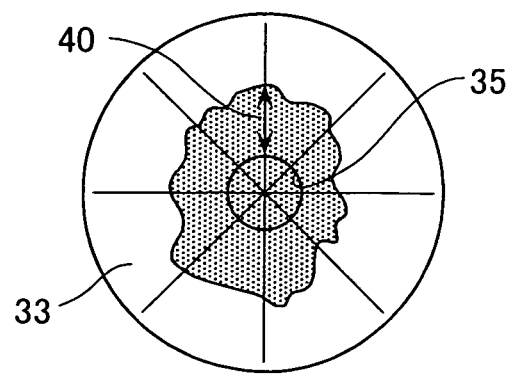
FIG. 25 is an explanatory view showing a measurement method for a water mobility value in the invention.

The water mobility value is a value showing an amount of excessive water in the heat-generating composition that can be moved outside the composition. The water mobility value will be described with reference to FIGS. 21 to 25. As shown in FIG. 21, No. 2 filter paper 33, on which eight lines extending from the center with intervals of 45° have been drawn, is placed on a stainless steel plate 37 as shown in FIGS. 22 and 23, and a template 34 having a hole 35 of a hollow cylinder shape having an inner diameter 20 mm and a height of 4 mm is placed on the center of the filter paper 33. A sample 36 is placed in the vicinity of the hole 35 having a hollow cylinder shape, and a pressing plate 30 is moved along the template 34, so as to place the sample 36 into the hole 35 having a hollow cylinder shape with pressing (press molding). Furthermore, as shown in FIG. 24, the hole 35 of a hollow cylinder shape having the sample 36 therein and the periphery thereof are covered with a wind guard 38, and they are maintained for 5 minutes. Thereafter, the filter paper 33 is brought out (FIG. 25), and the excursion of soaking water or an aqueous solution is read as distance 40 from the circumference part, which is an edge of the hole 35, to the front edge of soaking along the radial like in terms of mm units. The distances 37 along the respective lines are read to obtain eight values in total. The thus-read eight values are designated as measured water content values (a, b, c, d, e, f, g and h).

An arithmetic average of the eight measured water content values is designated as a water content value (mm) of the sample.

A water content for measuring the true water content value is a blended water amount of the heat-generating composition corresponding to the weight of the heat-generating composition having an inner diameter of 20 mm and a height of 4 mm, and the measurement is carried out by using only water corresponding to the water amount to obtain a true water content value (mm) through the similar calculation. A value obtained by dividing the water content value by the true water content value is multiplied with 100 to obtain the water mobility value.

That is, water mobility value=(water content value (mm)/true water content value (mm))×100.

The water mobility value herein is a value upon lamination, for example, by pressing molding or the like.

The water mobility value (0 to 100) of the heat-generating composition of the invention is generally from 3 to 50, preferably from 4 to 35, and more preferably from 6 to 20. In the case where it is less than 3, when the composition is laminated on a base material through a mold, it cannot be laminated due to poor flowability, and in the case where it exceeds 50, the composition runs off the mold shape to fail to maintain the shape.

The incremental degree of viscosity shows a difference between a BH type viscosity (BII type) S of the heat-generating composition containing a heat-generating substance, a carbon component, an oxidation accelerator and water, and a BH type viscosity (BH type) T of a heat-generating composition obtained by adding other substances thereto, and the value T-S is generally less than 1,000 cP (centipoise), preferably less than 500 cP, and more preferably less than 300 cP, which includes 0 and a negative value. There is no limitation in the negative value, and thus the viscosity may be decreased by any extent. As the BII type viscosity, such a value is employed that is obtained by placing a No. #7 rotor at 2 rpm in a center of a sample to obtain a value in a stable state after lapsing 5 minutes or more from the start of rotation. A BH type viscometer (BII type) with a #7 rotor at 2 rpm has a full scale 2,000,000 cP.

In the case where the value T-S is 1,000 cP or more, adverse influences occur in heat-generating characteristics, such as considerable deterioration in heat-generating property.

The heat-generating composition used in the invention is not particularly limited as far as it is non-viscous, has excessive water, causes a heat-generating reaction in the presence of air at least after charged in a heat-generating body, and forms a formed article having a shape retaining degree of 70 or more. According to the configuration, the formed article of the heat-generating composition charged as the heat-generating body can retain the shape of the formed article of the heat-generating composition unless the pressure inside the container bag is the same as that of the outside, whereby a heat-generating body excellent in use feeling can be obtained.

The heat-generating composition used in the invention is formed by using water as a binder to be non-viscous and to have flowability, and it is a non-viscous heat-generating composition having a water mobility value of from 3 to 50 and an incremental degree of viscosity (at a temperature of 20° C.) of less than 1,000. The incremental degree of viscosity is preferably less than 500 cP, and more preferably 300 cP. In the case where the incremental degree of viscosity of the heat-generating composition exceeds 1,000 cP, the heat-generating property is deteriorated to fail to generate heat or to lower the heat generation, whereby the practical application range is restricted, or no practicality is obtained.

The non-viscous heat-generating composition is a heat-generating composition containing, as essential components, a heat-generating substance, a carbon component, an oxidation accelerator and water, and examples thereof include a heat-generating composition obtained by adding, to the heat-generating composition, at least one kind selected from a water retaining agent, a water absorbing polymer, a pH adjusting agent, a hydrogen generation suppressing agent, a surface active agent, a defoaming agent, such as a fluoroalkyl group-containing silicone compound, a hydrophobic polymer compound, such as polyethylene, polypropylene, polyester, a pyroelectric substance, such as tourmaline, a far infrared ray radiating substance, such as ceramics, zeolite, a negative ion generating substance, such as granite, an aggregate, such as silica-alumina, a fibrous material, such as pulp, synthetic fibers, a thickener, such as poly-N-vinylacetamide, gelatin, a binder, such as sodium silicate, a separation stabilizer, such as CMC, a fertilizer component having a compound containing phosphorous, potassium or nitrogen, such as sodium phosphate, potassium chloride, urea, and a heat-generating assistant, such as triiron tetraoxide, and such a heat-generating composition that is formed by controlling the heat-generating composition in heat-generating reaction with excessive water.

That is, the mixing ratios in the non-viscous heat-generating composition used in the invention are not particularly limited, and it is preferred to use, per 100 parts by weight of the heat-generating substance, from 0.01 to 10 parts by weight of a water absorbing polymer, from 1.0 to 50 parts by weight of a carbon component, from 0.1 to 10 parts by weight of a reaction accelerator, from 0.01 to 10 parts by weight of a water retaining agent, from 0.01 to 5 parts by weight of a pH adjusting agent, from 0.01 to 5 parts by weight of a surface active agent, from 0.01 to 5 parts by weight of a defoaming agent, from 0.01 to 5 parts by weight of a hydrogen generation suppressing agent, from 0.01 to 10 parts by weigh each of a pyroelectric substance, a far infrared ray radiating agent and a negative ion generating substance, from 0.01 to 10 parts by weight each of a hydrophobic polymer compound, an aggregate and a fibrous material, from 0.01 to 10 parts by weight of an antioxidant, from 0.01 to 10 parts by weight of a fertilizer component, from 0.01 to 10 parts by weight of a heat-generating assistant, and from 0.001 to 0.25 part by weight of a syneresis preventing stabilizer. Furthermore, such a composition is also exemplified that is formed by further mixing from 20 to 60 parts by weight of water to make a totally non-viscous state having flowability. Furthermore, depending on necessity, from 0.01 to 10 parts by weight of a thickener, from 0.01 to 10 parts by weight of a binder, and from 0.01 to 3.0 parts by weight of a water soluble polymer are preferably used.

The water absorbing polymer largely varies in water permeability or liquid permeability associated with the difference in water absorbing property or liquid absorbing property depending on the water absorbing polymer used. Accordingly, the moldability, the shape maintenance property and the heat-generating property of the heat-generating composition having excessive water largely vary, and thus the nature of the heat-generating body also largely vary, depending on the water absorbing polymer used. In order to resolve the same in the invention, a liquid permeation degree has been introduced. The liquid permeation degree is preferably 15 or more in order to maintain at high levels the moldability, the shape maintenance property and the heat-generating property of the heat-generating composition having excessive water and a formed article thereof.

The average particle diameters of the respective water insoluble solid components are not particularly limited as far as the moldability and the shape maintenance property are retained, and is preferably 200 μm or less, more preferably 180 μm or less, and further preferably 150 μm or less. In the case where it exceeds 200 μm, the application range of the heat-generating body thus produced is narrowed from the standpoint of shape maintenance property.

A heat-generating body for warming foot of the invention constituted with a multilayer structure is a heat-generating body for warming foot having a two-layer structure or a layer structure having three or more layers, which have different compositional ratios except for water.

That is, assuming that respective layers constituting the multilayer structure are layer A to layer E, it is a heat-generating body for warming foot having a multilayer structure of two or more layers containing an appropriate combination thereof.

The layer A is a heat generation reaction layer containing at least a heat-generating substance and having a heat generation reaction as a major function.

The layer B is a heat generation reaction layer containing at least a heat-generating substance and having at least a compositional ratio that is different from the layer A and having a heat generation reaction as a major function.

The layer C is a reaction assistant layer containing no heat-generating substance and has a function, such as water absorption, other than the heat generation reaction as a major function.

The combination of the layers is not particularly limited, and examples thereof include the following multilayer structures.

Layer B/Layer A/(base material)
Layer B/Layer A/Layer C/(base material)
Layer B/Layer B/Layer A/Layer C/(base material)
Layer C/Layer A/Layer B/(base material With respect to the adjacent layers, layer A/layer B, herein, the case where the layer A is continuously changed to the layer B is also designated as the two-layer structure of the layer A and the layer B, as far as the compositional ratios of the layer A and the layer B are definitely different from each other.

Furthermore, the case where a mixed layer of the components of the layer A and the layer B is present between the layer A and the layer B is also designated as the two-layer structure of the layer A and the layer B. Hereinafter, it is similar for combinations of the other layers.

Similarly, multilayer structures formed by combining from the layer A to the layer C can be appropriately applied, and multilayer structure of a five-layer structure, a six-layer structure, a seven-layer structure and more can be applied.

The layers constituting the heat-generating multilayer laminated article may be formed by mixing components appropriately selected from a heat-generating substance, such as iron powder, a carbon component, such as activated carbon, a reaction accelerator, such as sodium chloride, water, a water retaining agent, a water absorbing polymer, a pH adjusting agent, a hydrogen generation suppressing agent, a surface active agent, a defoaming agent, a hydrophobic polymer compound, a pyroelectric compound, a far infrared ray radiating substance, a negative ion generating substance, an antioxidant, an aggregate, a fibrous material, a thickener, a binder, a separation stabilizer, a fertilizer component and a heat-generating assistant, and a surface of the heat-generating composition having an arbitrary formulation thus laminated may be partially oxidized by using irradiation of an infrared ray, heating or air blowing, so as to form a new layer.

Specific examples thereof include a heat-generating body for warming foot having two-layer structure having a layer A formed with a heat-generating composition containing iron powder, activated carbon, wood powder and water, and a layer B formed with a water absorbing polymer, and a heat-generating body for warming foot having a two-layer structure having a layer A formed with a heat-generating composition containing iron powder, activated carbon, wood powder and water, and a layer B formed with a layer obtained by treating the surface of the layer A with hot air. In particular, a heat-generating body having a heat-generating formed article having at least one layer of a water absorbing material, such as the heat-generating body for warming foot having the two-layer structure having a layer B formed with a water absorbing polymer can produce a heat-generating body that substantially attain heat generation in the case where a water nonabsorbing packing material, such as a base material, a covering material, a laying material formed with a water nonabsorbing material, is used, and the body is made in contact with air through an air permeable part.

While an organic material may be used as the heat-generating substance in the invention, iron powder, zinc powder, aluminum powder, magnesium powder, alloy powder containing two or more kinds of these metals, mixed metal powder formed by mixing two or more kinds of them, and the like, which do not form abnormal odor upon reaction, and in particular, iron powder is preferably used among these kinds of metallic powder from the standpoint of safety, handleability, cost, storage property, stability and the like.

The iron powder may be any kind that contains an iron element, and examples thereof include cast iron powder, atomized iron powder, electrolytic iron powder, reduced iron powder and the like. Furthermore, those formed by adding carbon to the iron powder, and those formed by mixing or mixing and attaching carbon to the iron powder are also useful.

The reaction accelerator may be any material that can accelerate oxidation of the heat-generating substance. Examples thereof include a metallic halogenide, such as sodium chloride, potassium chloride, magnesium chloride, calcium chloride, ferrous chloride, ferric chloride, cupric chloride, manganese chloride, cuprous chloride, a metallic sulfate, such as potassium sulfate, sodium sulfate, magnesium sulfate, calcium sulfate, copper sulfate, ferrous sulfate, ferric sulfate and manganese sulfate, a nitrate, such as sodium nitrate, potassium nitrate, an acetate, such as sodium acetate, and a carbonate, such as ferrous carbonate. These may be used solely or in combination.

The oxidation accelerator is generally used in the form of an aqueous solution and may also be used in the form of powder as it is.

The water may be one from a suitable source. The purity and the kind thereof are not limited.

The carbon component is not particularly limited as far as it contains a carbon component as a major component, such as carbon black, charcoal powder, peat charcoal, graphite, activated carbon. Activated carbon prepared from husks of coconuts, wood, charcoal, coal, bone charcoal or the like is useful. The species of the activated carbon to be used is not limited, and activated carbon exerting excellent adsorption maintenance property is preferred.

The performance of the carbon component is preferably an iodine absorbing capability of from 400 to 1,200 mg/g and a methylene blue decoloring capability of from 40 to 300 mg/g, and more preferably an iodine absorbing capability of from 800 to 1,200 mg/g and a methylene blue decoloring capability of from 100 to 300 mg/g.

A mixture of the carbon may be used in the invention.

The hydrogen generation suppressing agent may be any material that suppresses generation of hydrogen, and examples thereof include a sulfur compound, such as sodium sulfite, sodium thiosulfite, sulfur, sodium silicate and the like, as well as a combination thereof. A combination thereof with an oxidizing agent, such as manganese dioxide, may be also used.

Examples of the pH adjusting agent include an alkaline substance, as well as a carbonate of an alkali metal, a bicarbonate of an alkali metal, a phosphate of an alkali metal, a bicarbonate, a carbonate of an alkaline earth metal, a hydroxide of an alkali metal, a hydroxide of an alkaline earth metal and the like. Specific examples thereof include a hydroxide, such as sodium hydroxide, potassium hydroxide, magnesium hydroxide, calcium hydroxide, a carbonate, such as sodium carbonate, potassium carbonate, calcium carbonate, magnesium carbonate, strontium carbonate, a bicarbonate, such as sodium bicarbonate, potassium bicarbonate, and a phosphate, such as sodium tripolyphosphate.

These may be used solely or in combination thereof.

Examples of the surface active agent include a nonionic surface active agent, such as polyoxyethylene alkyl ether, an anionic surface active agent, such as sodium dodecylbenzenesulfonate, a cationic surface active agent, such as long-chain alkyl quaternary ammonium salt, and an amphoteric surface active agent, such as alkylamine oxide.

The water retaining agent is not particularly limited as far as it has high water holding property, and specific examples thereof include wood powder, vermiculite, zeolite, terraballoon, Shirasu balloon, perlite, cristobalite, a silica series porous substance, a silicate, such as calcium silicate, aluminum oxide, such as silica rock, diatom earth, alumina, aluminum oxide silicate, such as mica powder, clay, magnesia silicate, such as talc, silica powder, pulp powder, vegetable fibers and the like.

The particle diameter of the water retaining agent may be any value as far as it can be formed, and is preferably 950 μm or less, and it is more preferred that 50% or more of particles have a particle diameter of 150 μm or less, and further preferably 70% or more of particles have a particle diameter of 150 μm or less.

The water absorbing polymer is not particularly limited as far as it smoothly absorbs a large amount, i.e., twice the own weight or more, of water or an aqueous solution of a metallic chloride or the like, and such a water absorbing polymer is particularly preferred that is adjusted in crosslinked bonds to control the solubility to water or an aqueous solution of a metallic chloride or the like, and is not increased in viscosity in the heat-generating composition. In particular, that having a water absorbing power of 5 times or more in a 11% saline aqueous solution is preferred.

Examples thereof include crosslinked polyalkylene oxide, a N-vinylacetamide crosslinked product, an isobutylene-maleic anhydride copolymer, a starch-acrylate salt graft copolymer, a starch-polyacrylonitrile copolymer, a polyacrylate salt crosslinked product, an acrylate salt-acrylate ester copolymer, a polyacrylate salt-acrylamide copolymer, a hydrolysate of a polyacrylonitrile crosslinked product, a crosslinked polyacrylene oxide, a saponified product of a vinyl ester-styrene series unsaturated carboxylic acid copolymer, a reaction product of a polyvinyl alcohol series polymer and a cyclic anhydride, a polyvinyl alcohol-acrylate salt copolymer, and the like. These may be used solely or as a mixture of two or more kinds thereof. Furthermore, these may be treated with a surface active agent or may be combined with a surface active agent, so as to improve the hydrophilicity.

The syneresis preventing stabilizer may be any material that disperses the components of the heat-generating composition and prevents separation of water to retain dispersion state stably, and may be either an inorganic matter or an organic matter, and examples thereof include a water soluble polymer (such as those having at least one of an OH group, a carboxyl group and a sulfone group), a saccharide (such as a monosaccharide, an oligosaccharide and a polysaccharide), an aggregating agent, an aqueous dispersion emulsion and the like. A single kind of or plural kinds of syneresis preventing stabilizers may be simultaneously or separately added.

Examples of the water soluble polymer compound include a natural polymer, a semisynthetic product and a synthetic product.

Examples of the natural polymer include a starch series (a starch derivative), a syrup series, a mannan series, a seaweed series, a vegetable mucic matter, a mucic matter from microorganisms, a protein series, a polysaccharide series and the like, and specific examples thereof include starch, cone starch, dextrin, α-starch, cone syrup, (non-)crystalline sorbitol syrup and a mixture thereof, mannan paste, laver, agar (galactan), alginic acid, sodium alginate, gum arabic, be an gum, glue, gelatin, casein, collagen, albumin, pectin and the like.

Examples of the semisynthetic product include a cellulose series and a starch series, and examples of the cellulose series include viscose, methyl cellulose (MC), ethyl cellulose (EC), hydroxyethyl cellylose (HEC), carboxymethyl cellulose (CMC), sodium carboxymethyl cellulose, carboxymethyl-ethyl cellulose (CMEC), ethyl cellulose acetate, hydroxypropyl cellulose (HPC) and the like.

Examples of the starch series include soluble starch, carboxymethyl starch (CMS), carboxylated starch and the like.

The synthetic product include a polyoxyalkylene, such as polyvinyl alcohol, polyethylene oxide, polyethylene glycol, polyvinyl methylene ether, a polymaleic acid copolymer, polyvinyl acetate, a partially saponified product of polyvinyl acetate, polyvinyl acetal, polyurethane, water soluble urethane, an acrylsulfonic acid series polymer substance, poly-N-vinylacetamide, glycerin and the like, as well as a mixture of two or more of them.

The aqueous dispersion emulsion may be any material as far as it is in an emulsion form and has particle binding property, and in general, those obtained by forming a polymer compound to be a adhesive agent (cohesive agent) into an emulsion are used.

Examples thereof include an aqueous adhesive agent, a tackifier emulsion and the like.

Examples of the aqueous adhesive agent include an adhesive emulsion formed by adding a tackifier (adhesiveness imparting resin) emulsion, such as a rosin compound series resin emulsion, a petroleum resin emulsion, to an aqueous emulsion resin.

Examples of the aqueous emulsion resin include an emulsion of an acrylic polymer, a vinyl acetate series emulsion, such as polyvinyl acetate emulsion, a vinyl acetate-acrylate ester series emulsion, a urethane series emulsion, such as polyurethane emulsion, a styrene resin series emulsion, such as a styrene-butadiene copolymer emulsion, and a rubber latex, such as natural rubber, synthetic rubber.

Examples of the synthetic rubber latex include a nitrile rubber latex, a polybutadiene latex, a styrene-butadiene latex and the like.

Examples thereof include one kind selected therefrom and a combination of two or more thereof.

The thickener may be such a material that mainly absorb water or an aqueous solution of a metallic chloride to increase the viscosity or to impart thixotropy, and examples thereof include an ordinary substance having thickening effect, such as bentonite, gum arabic, a vinyl polymer, dextrin.

Examples of the oxidation assistant include triiron tetraoxide, manganese dioxide, copper dioxide, ferrous chloride, ferric chloride and the like.

The defoaming agent is not particularly limited as far as it has defoaming effect, and examples thereof include a fluoroalkyl group-containing silicone compound and the like.

Examples of the hydrophobic polymer compound are not particularly limited as far as it is a polymer compound having hydrophobicity, and examples thereof include polyethylene, polypropylene, polyester and the like.

Examples of the pyroelectric substance include tourmaline.

The far infrared ray radiating substance is not particularly limited as far as it radiates a far infrared ray, and examples thereof include ceramics, zeolite and the like.

The defoaming agent is not particularly limited as far as it has defoaming effect, and examples thereof include a fluoroalkyl group-containing silicone compound and the like.

The negative ion generating substance is not particularly limited as far as it generates a negative ion, and examples thereof include tourmaline, granite and the like.

Examples of the aggregate include silica-alumina and the like.

The fibrous material is not particularly limited as far as it is fibrous, and examples thereof include pulp, synthetic fibers and the like.

The thickener is not particularly limited as far as it has thickening effect, and examples thereof include poly-N-vinylacetamide, gelatin and the like.

Examples of the binder include sodium silicate and the like.

Examples of the fertilizer component include a compound containing phosphorous, potassium or nitrogen, such as sodium phosphate, potassium chloride, urea and the like.

Examples of the heat-generating assistant include triiron tetraoxide, copper, tin and the like.

It is possible that a polymer is provided on a laminated product of the heat-generating composition of the invention in a mesh form by melt-blowing, coating, spraying, coating or the like, so as to ensure the fixation of the heat-generating composition with the packing material, such as the base material, the covering material. Preferred examples of the polymer herein include a thermoplastic polymer compound, an emulsion series adhesive agent, a hot-melt series cohesive agent and the like.

The air permeable container bag having a formed article of the heat-generating composition charged therein may be any material that retains the mixture inside the bag, prevents the raw materials from leaking upon using the heat-generating bag, has such a sufficient strength that causes no possibility of breakage of the bag, and has air permeability necessary for heat generation, and in general, a container bag having air permeability formed by using a packing material such as a base material, a covering material in a film form, a sheet form or a nonwoven fabric form is used. Furthermore, it is more preferred that the packing material has water absorbing property.

In order that migration and deviation of the heat-generating composition are further prevented, it is possible that concave and convex parts are provided on at least one kind of the base material and the covering material or on a part of the one kind, and the heat-generating composition is provided at least on the concave part, or in alternative, concave and convex parts are provided on at least a part of at least one kind of the base material, the covering material and the heat-generating composition, and at least a part of the base material and the covering material may be adhered or tacked to at least a part of the heat-generating composition. A foamed film or sheet, paper, a nonwoven fabric, a woven fabric, a porous film or sheet, and a film, a sheet or a nonwoven fabric material formed with a water absorbing material can also be used. In the case where it is formed with a material having no water absorbing property, it may contain, may be impregnated with, may be kneaded with, may be transferred with, may be laminated with, or carries a water absorbing agent, so as to exert water absorbing property. It is needless to say that concave and convex parts may be formed on the base material and/or the covering material having water absorbing property.

The container bag produced from the base material and the covering material of the invention is constituted in such a manner that the base material and the covering material are sealed on the periphery of the heat-generating composition in the container bag by cohesion, heat fusion, press cohesion or heat press cohesion.

In the case of the cohesion, an cohesive that is ordinarily employed may be used.

In the case where heat fusion, i.e., heat sealing, is carried out, heat sealing may be carried out by providing a hot-melt cohesion layer formed with a hot-melt adhesive.

In the case of adhesion, press cohesion or heat press cohesion is carried out by using a cohesive agent.

The similar procedures may be applied to a container bag produced by using at least one kind of a base material, a laying material and a covering material.

The size and the shape of the container bag are not particularly limited, and may be any ones that can warm a foot, and examples thereof include a flat rectangular shape, a circular shape, a trapezoidal shape, a soleprint shape and the like.

Therefore, the thickness of the base material and the covering material largely varies depending on purposes and is not particularly limited. Specifically, it is generally from 5 to 5,000 μm, and in the case where it is used by directly attached to a foot, is preferably about from 10 to 1,500 μm, and particularly from 20 to 1,000 μm, and in general, it is preferably from 5 to 2,500 μm, and particularly from 10 to 2,000 μm.

In the case where the thickness of the base material and the covering material is less than 5 μm, it is not preferred since there is such a possibility that the necessary mechanical strength cannot be obtained, and the thickness is difficult to be uniform.

In the case where the thickness of the base material and the covering material exceeds 5,000 μm, it is also not preferred since the flexibility is deteriorated to lower the followability to deformation and movement of the surface of the foot by lowering the fit to the surface of foot remarkably, it becomes stiff to deteriorate the texture, and the total thickness of the heat-generating body for warming foot becomes too large.

The air permeability of the part having air permeability of the base material, the covering material, the packing material and the container bag is not limited as far as the heat-generating property is retained since it varies depending on purposes, and it is preferred for an ordinary product for warming foot that the moisture permeability in terms of the Lyssy method (Lyssy method Model L80-4000H) is in a range of from 50 to 10,000 $g/m^2 \cdot 24$ hr.

In the case where the moisture permeability is less than 50 $g/m^2 \cdot 24$ hr, it is not preferred since the heat generation amount is small to fail to obtain a sufficient heating effect, and in the case where it exceeds 10,000 $g/m^2 \cdot 24$ hr, there is a possibility that the heat generation temperature is increased to cause a problem on safety.

The air permeability of the part having air permeability of the base material, the covering material, the packing material and the container bag is preferably in a range of from 1 to 100 seconds per 100 mL in terms of air permeability by the Gurley method.

In the case where the air permeability exceeds 100 seconds per 100 mL, it is not preferred since the heat generation amount is decreased to fail to obtain sufficient heating effect, and in the case where it is less than 1 second per 100 mL, it is not preferred since there is a possibility that the heat generation temperature is increased to cause a problem on safety, and the heat generation time is shortened.

The region having air permeability may be any one that has air permeability. It may be constituted with regions different in air permeability, and regions different in air permeability may be repeated twice or more in a pattern, such as a dotted pattern, a stripe pattern.

The region having air permeability may be constituted with a water absorbing air permeable material having water absorbing property, and examples of the material include paper, a water absorbing nonwoven fabric or a woven fabric formed with rayon or the like, and the like.

In the case where the excessive water is absorbed by the housing body, the water absorbing amount of the base material, the covering material, the packing material and the container bag is not particularly limited as far as water absorption can be carried out, and it is preferably 1 $g/m^2$ or more, more preferably from 5 to 1,000 $g/m^2$, further preferably from 10 to 650 $g/m^2$, and particularly preferably from 12.5 to 550 $g/m^2$.

In order to improve the usability of the container bag formed with the base material and the covering material upon use, an adhesive agent layer or an antislipping layer may be provided. In the case where the one surface thereof has an air permeable part, and the other surface is formed with an air nonpermeable material, an adhesive layer is provided on a whole or a part of the air nonpermeable side. Furthermore, in the case where the adhesive agent layer is provided, releasing paper may be superposed thereon until subjecting to use to prevent from cohesion to another member. The heat-generating bag thus obtained is sealed and stored in an air nonpermeable bag to prevent from contact with oxygen in air.

An air permeable adhesive agent layer may be provided instead of the air nonpermeable part, and it is also possible that both surfaces are air permeable parts, and an air permeable adhesive agent layer is provided on the air permeable part on at least one surface.

Moreover, the base material, the covering material, the adhesive agent layer and the antislipping layer used in the invention may contain, depending on necessity, at least one kind selected from a water retaining agent, a water absorbing polymer, a pyroelectric substance, such as tourmaline, a far infrared ray radiating substance, such as ceramics, a negative ion generating substance and a medical drug.

The packing material, such as the base material, the covering material, used in the heat-generating body for warming foot of the invention may be a single layer material and a material formed by laminating plural layers in the thickness direction. In this case, the lamination means that the layers are overall or partly connected by heat-setting, cohesion, adhesion, lamination or the like, or the respective layers are simply superimposed, and the layers are connected at spots, such as a periphery part, a central part, with a heat-sealing agent, a hot-melt cohesive, an adhesive agent or the like.

Examples of the packing agent for warming foot of the invention include a single layer air permeable water nonabsorbing packing material, a single layer air nonpermeable water absorbing packing material, a single layer air permeable water nonabsorbing packing material, a single layer air permeable water absorbing packing material, a multilayer air nonpermeable water nonabsorbing packing material, a multilayer air nonpermeable water absorbing packing material, a multilayer air permeable water nonabsorbing packing material and a multilayer air permeable water absorbing packing material, and in order to prevent the heat-generating composition from leakage and contamination upon application pressure during use, a multilayer air nonpermeable water absorbing packing material, a multilayer air permeable water nonabsorbing packing material and a multilayer air permeable water absorbing packing material are preferred. The water absorbing property also includes water retaining property.

The air nonpermeable packing material is not particularly limited as far as it is air nonpermeable, and examples of the single layer air nonpermeable packing material include a film or a sheet of a polymer and a foamed material having closed cells.

The multilayer air nonpermeable packing material may be any multilayer packing material that contains the single layer air nonpermeable packing material, and examples of the laminated layer structure of the multilayer air permeable packing material include a laminated body having an appropriate combination of T with materials A to E with possible duplications and X connecting the layers, in which:

T: polymer film
T1: polymer film formed by extruding lamination
A: nonwoven fabric
B: foamed sheet with closed cells
C: paper or paperboard
C1: perforated paper or paperboard
C2: paper or paperboard with dimples
D: woven fabric or silk cloth
X: adhesive (cohesive) agent layer.

Examples of the laminated layer structure include:
T/X/C, T/X/C/X/A, B/X/T/X/C,
B/X/C,
T/X/C1, T/X/C1/X/A, B/X/T/X/C1,
B/X/C1,
T/X/C2, T/X/C2/X/A, B/X/T/X/C2,
B/X/C2,
T1/C, T1/C/A, B/T1/C, B/C,
T1/C1, T1/C1/A, B/T1/C1, B/C1,
T1/C2, T1/C2/A, B/T1/C2 and B/C2.

Examples of the air permeable packing material include one with air permeability by providing fine pores with a needle or the like on an air nonpermeable packing material formed by laminating a polyethylene film with a nonwoven fabric, a nonwoven fabric controlled in air permeability by laminating fibers by heat press cohesion, a fine porous film, a material formed by adhering a fine porous film with a nonwoven fabric, and the like, and examples of the laminated layer structure of the multilayer air permeable packing material constituting the air permeable part of the multilayer air permeable packing material include a laminated body having an appropriate combination of more than two of materials A to E with possible duplications and X connecting the layers, in which:

A: nonwoven fabric
B: air permeable foamed sheet, woven fabric or silk cloth
C: paper or paperboard, woven fabric or silk cloth
D: porous film
E: perforated film
X: air permeable adhesive agent or air permeable cohesive layer.

Examples of the laminated layer structure include:
A/X/D/X/C,
A/X/C/X/D,
A/X/B/X/D,
A/X/D/X/C/A,
E/X/C/X/D, E/X/D/X/C,
B/X/C/X/D, B/X/D/X/C,
A/X/D, E/X/D, B/X/A/X/D and
B/X/E/X/D.

It is also possible that a nonperforated air nonpermeable film is used instead of E, and after forming the laminated body, the air nonpermeable film is perforated, or the entire laminated body is perforated, to form the multilayer air permeable packing material.

It is possible that a laminated body is formed by changing X to an air nonpermeable cohesive (adhesive) agent layer, and thereafter, the entire laminated body is perforated to form the multilayer air permeable packing material.

The cohesive (adhesive) agent layer can be formed with a hot-melt cohesive in the case of heat fusion, i.e., heat sealing, with an cohesive in the case of cohesion, and with an adhesive agent in the case of adhesion. The form of the respective layers may be either a dotted form, a linear form, a film form, a foamed sheet form or a nonwoven fabric form, with or without pores.

The method for constituting a part of the base material and the covering material with air permeable is not particularly limited, and examples thereof include such manners that:

(1) a porous film is used,
(2) such a film is used that is obtained by forming through pores on a material, such as paper, a porous film and an air nonpermeable film by using an ultrathin needle, a laser or the like,
(3) such a film or a sheet is used that has continuous cells opening on both front and back surfaces formed by foaming a polymer material,
(4) such a film or sheet is used that is formed in such a manner that a polymer material is foamed to form closed cells or continuous cells opening on both front and back surfaces, and after foaming, the film or sheet is pressed to break the closed cells or the continuous cells, whereby air permeable pores communicating with both front and back surfaces are formed, and
(5) an air permeable sheet having a laminated body containing a porous film is subjected to a heat embossing processing to cut the porous film, whereby relatively large pores are formed and/or the existing pores are enlarged.

The method for decreasing the air permeation degree of the base material and the covering material is not particularly limited, and examples thereof include such manners that:

(1) the air permeable part is partly, i.e., in a dotted form or a stripe form, heated or pressed under heating to form an air nonpermeable part sectionally, whereby the air permeation degree of the air permeable thermoplastic part is decreased, and
(2) an air nonpermeable resin, such as an adhesive agent, a cohesive, is partly provided on the air permeable part by a melt-blowing method, gravure printing or a coating method, so as to decrease the air permeation degree of the entire material.

An air permeable sheet having totally varied air permeation degrees with respect to regions can be formed by combining the foregoing methods, and can be used as the air permeable base material or the air permeable covering material. For example, it is possible that a nonwoven fabric is used as the air permeable base material or covering material, and such a heat-generating body as having a combination of nonwoven fabric/air permeable adhesive (cohesive) agent/heat-generating composition/nonwoven fabric, or a combination of air permeable covering material/nonwoven fabric/air permeable adhesive (cohesive) agent/heat-generating composition/nonwoven fabric/substantially air nonpermeable base material formed by covering the former combination with an air permeable covering material and a substantially air nonpermeable base material, followed by sealing the periphery thereof.

Paper, a foamed film or sheet, a nonwoven fabric and a porous film have air permeability by themselves, but depending on necessity, with a laser and a needle through pores, nonthrough pores or pore-like concave parts may be provided to form an antislipping part or water retaining pits for excessive water on the laminated material of the heat-generating composition.

Examples of the polymer include a polymer material, such as polyethylene, polypropylene, polyester, polyvinyl chloride, polyvinylidene chloride, polystyrene, a saponified product of an ethylene-vinyl acetate copolymer, an ethylene-vinyl acetate copolymer, polycarbonate, an aromatic or aliphatic polyamide, polysulfone, polyvinyl alcohol, polyacrylonitrile, a vinyl chloride-vinylidene chloride series resin, polyimide, hydrochloric rubber, polyphenylene oxide, polyphenylene sulfide, polyamideimide, an epoxy resin, polyaminobismaleimide, polyacetal, polyether ether ketone, polyether sulfone, polyarylate, polyoxybenzyl and the like, as well as copolymers containing them, a natural material, such as paper, pulp, fibers, cotton, and a woven fabric, a woven cloth, a nonwoven fabric, a film, a sheet, a foamed sheet and the like formed by combining them.

It is also possible that the packing material for the heat-generating body for warming foot is formed with a stretch base material and covering material, i.e., an extensible film or sheet, in particular, a stretch film or sheet, whereby it can further well follow a curved part, a stretch part and a bending and stretch part of a foot.

The stretch base material and covering material are not particularly limited as far as they are formed with a stretch material, and in particular, examples thereof include a foamed film or sheet, a nonwoven fabric, a woven fabric and a porous film or sheet having stretch property and having high affinity with the heat-generating composition. These may be water absorbing or water nonabsorbing.

The stretch material is not particularly limited as far as it is stretch. Examples thereof include a single material of natural rubber, synthetic rubber, an elastomer, a stretch shape-memory polymer or the like, a mixture or a mixed yarn of these materials with a nonstretch material, a woven fabric, a film, a spundex thread, a thread, a string, a flat plate, a ribbon, a slit film, a foamed material and a nonwoven fabric constituted with these combinations, a composite stretch material formed by lamination or the like of these materials or these materials with a nonstretch material, and the like.

A thermoplastic elastomer having thermoplasticity is preferred among the elastomers because it can be easily form a laminated body with a nonwoven fabric or the like. Furthermore, in the case where the stretch material is air nonpermeable, stretch property or extensible property and air permeability can be imparted thereto by opening pores by using such a measure for opening pores as a heat pin method, an embossing method and the like. That is, it is sufficient to have stretch property in total, and a single material and a composite product formed by combining stretch base materials or with a nonstretch base material can be used.

The synthetic rubber may be any material that has been generally known, and examples thereof include butadiene rubber, 1,2-polybutadiene, isoprene rubber, styrene-butadiene rubber, a styrene-butadiene-styrene copolymer and the like.

Examples of the thermoplastic elastomer include an olefin series elastomer, a urethane series elastomer, an ester series elastomer, a styrene series elastomer, an amide series elastomer, a silicone series elastomer and the like.

Examples of the olefin series elastomer include an ethylene-propylene copolymer, an ethylene-propylene-diene terpolymer, chlorosulfonated polyetyrene, chlorinated polystyrene, an ethylene-vinyl acetate copolymer and the like. Among these, an ethylene-α-olefin copolymer produced by using a cyclopentadienyl complex, i.e., a metallocene catalyst, is particularly preferred.

Examples of the urethane series elastomer include a urethane series elastomer formed with a block having a urethane bond and a block of a polycarbonate polyol, an ether polyol, a polyether polyester polyol or a caprolactone polyester.

In particular, a polyurethane film formed therefrom has such characteristics that it is nonporous and has moisture permeability with stretch property.

Examples of the ester series elastomer include an ester series elastomer formed with a block having an aromatic polyester and a block having an aliphatic polyester or an aliphatic polyether.

Examples of the stretch shape-memory polymer include a copolymer, such as a polyisoprene series, a styrene-butadiene series, a polyurethane series, a polymer alloy series.

Examples of the hot-melt adhesive include a thermoplastic resin, such as polyethylene, polypropylene, polyester, nylon.

These may be used solely or in appropriate combination thereof, and from the standpoint of covering workability by heat sealing, such a covering material and the like are preferred that is formed by arranging fibers or a film having a low melting point on the side in contact with a support, and arranging fibers or a film being non-melting or having a high melting point on the other side.

The porous film may be any material that is an air permeable film having fine pores with a pore diameter of about from 0.01 to 10 μm, and examples thereof include an air permeable film formed with a resin selected from a polyethylene resin including a linear low density polyethylene resin, a polypropylene resin, a polyethylene terephthalate resin and a hot-melt resin, generally having a thickness of from 10 to 500 μm, and preferably from 15 to 200 μm, and having fine pores with a pore diameter of about from 0.01 to 10 μm.

The porous film in the invention may be a single layer material or a material formed with two or more layers.

The paper used in the invention is not particularly limited, and examples thereof include paper and a paperboard. Examples of the paper include package paper, such as kraft paper, and general purpose paper, such as crepe paper, card paper, and examples of the paperboard include a corrugated fiberboard, a core of a corrugated fiberboard, such as a pulp core, a special core, a liner of a corrugated fiberboard, such as kraft, jute, building paper, such as base paper for a plaster board and the like.

Waterproof paper, waterproof and oilproof paper, waterproof heat-sealing waterproof paper, and heat-sealing waterproof and oilproof paper can also be used. For example, waterproof paper and waterproof and oilproof paper can be formed in such a manner that the foregoing paper or paperboard is coated, impregnated (externally added), internally added, subjected to lamination of a plastic film, or the like method, with a wet paper strengthening agent, such as a polyamide epichlorohydrin resin, a oilproof and waterproof agent, such as a fluorine resin, or a waterproof agent, such as an acrylic resin emulsion. Furthermore, heat-sealing waterproof paper and heat-sealing waterproof and oilproof paper can be formed by coating a nonthermoplastic resin emulsion, such as a crosslinked ionomer emulsion, on at least one surface of them to form a heat-sealing layer.

It is possible that through pores or non-through pores are formed on the paper, the paperboard or the waterproof paper with a laser, a needle or the like as desired to impart such a function as antislipping of the laminated material of the heat-generating composition and drainage or holding of excessive water.

Specific examples of the foamed sheet include a closed cell foamed sheet, a continuous cell foamed sheet and a foamed sheet having a mixture of closed cells and continuous cells formed with at least one kind selected from foamed polyurethane, foamed polystyrene, a foamed ABS resin, foamed polyvinyl chloride, foamed polyethylene and foamed polypropylene.

The cloth and the woven fabric are not particularly limited, and specific examples thereof include, in terms of fibers constituting them, natural fibers, regenerated fibers using a natural material, such as viscous fibers, semisynthetic fibers, synthetic fibers, a mixture of two or more of them, and the like.

Examples of the natural fibers include vegetable fibers, such as cotton, linen, and animal fibers, such as silk, animal hair, and examples of the polymer material constituting the synthetic fibers include polyethylene, polypropylene, polyamide, polyester, polyurethane and the like.

As the nonwoven fabric, those of water absorbing or water nonabsorbing formed with regenerated fibers, artificial fibers, such as synthetic fibers, semisynthetic fibers, natural fibers, and the like can be used.

The natural fibers are not particularly limited, and specific examples thereof include arboreous cotton, kapok, Manila fibers, sisal fibers, cotton, wool, mohair, cashmere, camel wool, alpaca wool and the like.

Examples of the artificial fibers include, regenerated fibers, semisynthetic fibers and synthetic fibers, examples of the regenerated fibers include viscous rayon, copper ammonia rayon and the like, examples of the semisynthetic fibers include acetate, and examples of the synthetic fibers include polyamide series synthetic fibers, polyester series synthetic fibers, polyvinyl alcohol series synthetic fibers, polyvinyl chloride series synthetic fibers, polyvinylidene chloride series synthetic fibers, acrylic series synthetic fibers, modacrylic series synthetic fibers, polyolefin series synthetic fibers, fluorocarbon series synthetic fibers, polyurethane series synthetic fibers and the like.

As a hydrophobic or water nonabsorbing nonwoven fabric, a nonwoven fabric of a polymer material can be used, and examples of the nonwoven fabric of a polymer material include a polyester nonwoven fabric, a polypropylene nonwoven fabric, a nonwoven fabric of polyester/polystyrene ES fibers, a composite nonwoven fabric of polyester and polyethylene, an adhesive polyurethane nonwoven fabric and the like.

As fibers constituting the woven fabric, natural fibers, regenerated fibers using a natural material, such as viscous fibers, semisynthetic fibers, synthetic fibers, a mixture of two or more kinds of them, and the like can be used.

In the case where the base material, the covering material and the container bag have water absorbing property, a water absorbing material constituting them is not particularly limited as far as it has water absorbing property and is in a film or sheet form, and specific examples thereof include a foamed film or sheet having water absorbing property, paper, a paperboard, such as a corrugated fiberboard, a core of a corrugated fiberboard, a nonwoven fabric, such as a rayon nonwoven fabric, a woven fabric and a porous film or sheet.

The water absorbing material is not particularly limited as far as it has water absorbing property as a result, whether or not the material itself has water absorbing property, and specific examples thereof include a foamed film or sheet having water absorbing property, paper, a paperboard, such as a corrugated fiberboard, a core of a corrugated fiberboard, a nonwoven fabric or a woven fabric formed with fibers having water absorbing property, such as a rayon nonwoven fabric, a material formed with a water absorbing material, such as a porous film or sheet having water absorbing property, a material obtained by containing, impregnating, kneading, transferring or carrying a water absorbing agent on a foamed film or sheet, paper, a nonwoven fabric, a woven fabric or a porous film or sheet to impart water absorbing property, and a material obtained by attaching a foamed film or sheet, paper, a nonwoven fabric, a woven fabric or a porous film or sheet having water absorbing property cut into a planar shape of the heat-generating composition to a foamed film or sheet, paper, a nonwoven fabric, a woven fabric or a porous film or sheet to impart water absorbing property.

It is preferred in the invention that a water absorbing agent is contained, impregnated, kneaded, transferred or carried on at least a part of the base material and/or the covering material in contact with the heat-generating composition, or the water absorbing material to form a water absorbing layer, so as to lay or connect a whole or a part of the heat-generating composition to concave and convex parts thereof and/or the water absorbing layer, whereby migration and deviation of the heat-generating composition is further prevented.

Furthermore, it is also possible that a part of water content of the heat-generating composition, i.e., the excessive water, is absorbed or held in the base material and/or the covering material with the concave part of the concave and convex parts and/or the water absorbing layer.

The heat-sealing agent may be any material that is a thermoplastic resin, and examples thereof include the foregoing polymers, an ethylene-acrylate ester copolymer resin, such as an ethylene-vinyl acetate copolymer resin, an ethylene-isobutyl acrylate copolymer resin, a polyamide series resin, a polyester series resin, a butyral series resin, a cellulose derivative series resin, a polymethyl methacrylate series resin, a polyvinyl ether series resin, a polyurethane series resin, a polycarbonate series resin, and vinyl acetate, a vinyl chloride-vinyl acetate copolymer.

Examples of the hot-melt cohesive agent include, an A-B-A type block copolymer, a polyolefin series resin or a polyolefin series copolymer and modified products thereof, and a single material or a mixture of two or more of them.

The modified product means such a material in that a part of the components of the hot-melt type polymer substance is replaced with another component, so as to improve the property of the hot-melt type polymer substance, such as the adhesive property of the hot-melt type polymer substance, or to change the stability and the like.

In the A-B-A type block copolymer, the block A is a monovinyl-substituted aromatic compound A, such as styrene, methylstyrene, which is a non-elastic polymer block, and the block B is an elastic polymer block of a conjugated diene, such as butadiene, isoprene. Specific examples thereof include a styrene-butadiene-styrene block copolymer, a styrene-isoprene-styrene block copolymer and the like, and these may be used after mixing, with those mixed with various kinds of antioxidants being also exemplified.

The adhesive agent for forming the adhesive agent layer may be any material of either an emulsion type, a solvent type or a hot-melt type, as far as it has such a fixing capability that the heat-generating body for warming foot can be fixed to a prescribed part with the adhesive force, and examples of the adhesive agent include a vinyl acetate series cohesive agent, a polyvinyl alcohol series adhesive agent, a polyvinyl acetal series adhesive agent, a vinyl chloride series adhesive agent, an acrylic series adhesive agent, a polyamide series adhesive agent, a polyethylene series adhesive agent, a cellulose series adhesive agent, a chloroprene (neoprene) series adhesive agent, a nitrile rubber series adhesive agent, a polysulfide series adhesive agent, a butyl rubber series adhesive agent, a silicone rubber series adhesive agent, a hot-melt type styrene elastomer series adhesive agent (such as SIS, SBS, SEES (a hydrogenated type of SBS), SIPS (a hydrogenated type of SIS) and the like), and the like.

The antislipping layer in the invention is not particularly limited as far as it has an antislipping effect, and it is possible that the antislipping agent is provided on a whole surface of the air nonpermeable part of the heat-generating body for warming foot, a porous resin formed by making the antislipping agent into fibers is provided on the heat-generating body for warming foot, a porous weakly adhesive layer on a separator is transferred and fixed to the surface of the heat-generating body for warming foot, or it may be provided directly on the surface of the heat-generating body for warming foot in a spider-web form by a melt-blowing method or the like. It is also possible that a film of a foamed polyurethane or a polyolefin series resin polymerized with a metallocene catalyst is laminated, a polyolefin series resin is laminated or printed in solids or a pattern form, or a weakly adhesive substance or a soft vinyl chloride resin in a particulate form is uniformly dispersed and fixed by heating to form a large number of protrusions. Such a configuration can also be used in that a solution, a dispersion or a plastisol of an elastomer is diffused in a stripe form or a dotted form. The antislipping layer may be provided overall or partly on the heat-generating body for warming foot in such a range that the function as a heat-generating body is not inpaired, and adhesion between the antislipping agent and the base material may be improved by application of heat or pressure with a roll or the like. Any kind of the antislipping agent including a hot-melt series, a solvent series, an emulsion and the like may be used. It is also possible that a film, a sheet or a foamed sheet containing the same may be attached.

The antislipping agent may be any material that has an antislipping effect, and examples thereof include a adhesive agent and a weakly adhesive substance.

Examples of the weakly adhesive substance include a styrene series elastomer, such as SIS, SBS, SEES and SIPS, an acrylic series elastomer having an alkyl ester component, such as an acrylic acid series and a methacrylic acid series, an olefin series elastomer, a urethane series elastomer and the like.

Other examples of the antislipping agent include a soft vinyl chloride resin, natural rubber, styrene-butadiene rubber, urethane rubber, and a material obtained by mixing a binder resin with capsules formed by containing a foaming agent (a volatile foaming agent, such as isobutane) in a core of a resin, such as an ethylene-vinyl acetate copolymer (such as acrylic resin) and the like. Furthermore, an adhesiveness imparting agent, such as a petroleum resin, may be added to adjust the adhesiveness.

A medical drug contained in the medical drug-containing layer may be any substance as far as it has medical benefits, and examples thereof include one kind or a mixture of two or more kinds of a perfume material, such as peppermint, lavender oil, a transdermal absorption agent such as a ginger extract, a herbal medicine, salicylic acid and indomethacin, a disinfectant, an antifungal agent, an odor eliminating agent and a deodorizing agent.

The production process of the invention will be described in detail below.

The production process of the invention is a process for producing a heat-generating body for warming foot containing steps of: laminating a sherbet heat-generating composition on at least one prescribed region on an upper surface of a base material in a film form or a sheet form in a shape covering an arbitrary part of a foot, and overlaying a covering material to cover the laminated material. More specifically, a non-viscous heat-generating composition is laminated on a base material in a film form or a sheet form by mold-through forming, gravure printing or the like, and then a covering material in a film form or a sheet form is overlaid thereon, followed by adhering the base material and the covering material at a periphery of the laminated heat-generating composition and the laminated body is obtained. Thereafter, the assembly is punched to a size larger than the laminated body to produce the heat-generating body.

The heat-generating composition used in the production process of the invention is not particularly limited as far as it has moldability and shape maintenance property, and such composition is preferred that is formed with components causing a heat generation reaction upon reaction with oxygen in air, is non-viscous, is controlled in heat generation reaction with water, does not cause heat generation in air unless excessive water is removed from the heat-generating composition, and has such a nature that it flows upon application of an external force.

In particular, such a non-viscous and sherbet heat-generating composition is preferred that can be easily transferred or laminated by a technique, such as mold-through press molding, leveling molding, pressing and leveling molding, pressing and transferring molding, gravure printing.

It is possible that after forming the heat-generating composition on the base material, or after further overlaying the covering material thereon and arranging into a flat form by passing between rollers, at least a part of the base material, the covering material and the like is removed to obtain a heat-generating body for warming foot, or in alternative, they are left untouched, but the covering material and the base material are sealed, which are further charged in an outer bag formed with an air nonpermeable packing material, followed by sealing.

In the production process of the invention, an adhesive agent layer or an antislipping layer may be formed on a whole or a part of one of the exposed surfaces of the laminated body.

The process for producing a heat-generating body for warming foot of the invention will be described in detail with reference to examples, but the invention is not limited thereto.

The process for producing a heat-generating body for warming foot of the invention has a basic process of sequentially carrying a first step of a production step of a heat-generating composition, a second step of laminating the heat-generating composition on at least one prescribed region on an upper surface of a base material in a film form or a sheet form in a shape covering an arbitrary part of a foot, and a fourth step of overlaying a covering material to cover the laminated material. Furthermore, a step selected from a first step, a second step, a second step A, a second step B, a third step, a third step A, a third step B, a third step C, a fourth step, a fourth step A, a fifth step, a sixth step, a seventh step and an eighth step described below with possible duplications is arbitrarily inserted among the basic process depending on necessity.

First step: production of heat-generating composition
Second step: forming
Second step A: forming using leveling plate and magnet
Second step B: forming using pressing plate with vibrating device
Third step: lamination, diffusion or coating on heat-generating composition or the like
Third step A: provision of air permeable adhesive polymer
Third step B: lamination, diffusion or coating on base material or the like
Third step C: surface treatment of heat-generating composition
Fourth step: covering
Fourth step A: lamination (heat fusion, press adhesion, heat press adhesion or the like)
Fifth step: pressing
Sixth step: dehydration
Seventh step: punching Eighth step: housing heat-generating body for warming foot in air nonpermeable container bag The first step, the second step, the second step A, the second step B, the third step, the third step A, the third step B, the third step C, the fourth step, the fourth step A, the fifth step, the sixth step, the seventh step and the eighth step used in the invention are appropriately combined with possible duplications in random order to produce the heat-generating body of the invention.

For example, a production process can be constructed by carrying out the third step B, the first step, the second step B, the third step B, the third step A, the fourth step, the fourth step A and the seventh step in this order.

The atmospheres for the respective steps may be any of an atmosphere containing oxygen, such as air, and an inert gas atmosphere, such as nitrogen, argon, for preventing the iron powder from oxidizing by contacting with oxygen in air. These atmospheres can be appropriately introduced into the steps and can be combined to construct the production steps in total.

In the case where a magnet and a leveling plate are applied to the heat-generating composition, such a heat-generating body for warming foot can be obtained in that transferring or lamination can be easily carried out by printing or coating, and it has an ultrathin form with heat-generating property of a high speed and a long duration. Furthermore, in the case where the heat-generating composition thus laminated is pressed, such a heat-generating body for warming foot can be produced that has a further ultrathin form and a long-term heat-generating property. Moreover, since the excessive water functions as a barrier layer, the supply amount of air is decreased to terminate the heat-generating reaction in a substantial manner. As a result, heat generation loss upon production, deterioration in quality of the heat-generating composition and various problems associated with solidification of the heat-generating composition can be prevented, and further, excellent heat-generating property is exhibited owing to the excellent draining property. In the case where a water absorbing polymer is mixed, heat generation temperature characteristics of high performance can be obtained for a long period of time upon use owing to the high water holding property.

The respective steps will be described in detail.

In the first step, iron powder, activate carbon, an oxidation accelerator and water, as well as, depending on necessity, a dispersion stabilizer, a water retaining agent, a water absorbing polymer, a heat-generating assistant, a silicone resin, a hydrogen generation suppressing agent, a foaming agent and the like in prescribed amounts are mixed to prepare a sherbet composition.

The order of mixing is not particularly limited, and examples thereof include such operations that (1) all the components are placed in a mixing apparatus and then uniformly mixed, (2) the respective components are sequentially placed in a mixing apparatus and then sequentially and uniformly mixed, (3) only the solid contents among the all the components are divided into some groups, which are sequentially placed therein, and (4) all the solid contents are placed in a mixing apparatus and uniformly mixed in the mixing apparatus, and then water, an aqueous solution or dispersion of a metallic chloride is placed therein, followed by mixing.

The mixing apparatus used in the first step of the invention is not particularly limited as far as it can uniformly mix the components constituting the non-viscous heat-generating composition having excessive water, and specific examples thereof include a screw blender, a ribbon mixer, a spartan mixer, a roll mixer, a banbury mixer, a mixing and extruding screw and the like.

Upon producing the heat-generating composition of the invention, any mixing apparatus may be used as far as it can basically mix the raw materials constituting the heat-generating composition.

In the second step, the heat-generating composition obtained in the first step is formed into an arbitrary soleprint shape on at least one prescribed region on the base material or the laying material in a film form or a sheet form by mold-through forming, mold pressing forming or printing, such as gravure printing. Furthermore, specific examples thereof include the second step A and the second step B, which may be appropriately used. The base material and the laying material referred herein are the same as those described for the heat-generating body of the invention.

In the second step A, forming, such as mold pressing forming, mold-through transferring, lamination and the like, is carried out under application of vibration. The means for applying vibration may be any means that can apply vibration to the sherbet heat-generating composition of the invention, and examples thereof include a vibrating apparatus that is ordinarily employed using an eccentric motor, a piezoelectric element, air or the like.

In this case, pressing of the heat-generating composition with a pressing plate may be carried out. The pressing plate may be any article that can press the heat-generating composition of the invention into a mold, and is preferably formed with plastics, such as an acrylic resin, a vinyl chloride resin, polyethylene, a metal, such as iron, stainless steel, or a composite material thereof, examples of which include a plate having spring elasticity.

In the second step B, a cylinder head having an agitation device is used for imparting flowability to the heat-generating composition, and flowability is imparted to the heat-generating composition under agitation of the heat-generating composition supplied into the head, followed by supplying to the mold for a foot part. Vibration may be applied to the head at this time. The base material, the mold plate and a receiving plate for receiving them (such as a belt of a belt conveyer) are passed as a unit between a leveling plate provided by fixing in somewhat front (proceeding direction of the mold plate) of the head on a lower part and a magnet placed thereunder. The heat-generating composition is attracted on the base material through the mold with the magnet, and simultaneously, the surface of the heat-generating composition is leveled with the leveling plate along the mold for a foot part to accomplish molding. Thereafter, the mold is released from the base material. The magnet may be any one that has magnetism, and examples thereof include a permanent magnet and an electromagnet.

It is also possible that the mixing apparatus is simplified to a rotation bridge preventing apparatus, and a bridge caused upon supplying the heat-generating composition provided to the head to the mold is prevented.

In the second step C, a roll having a mold is attached to the cylinder head used in the second step B. The heat-generating composition is supplied from the head to the roll, and the surface of the heat-generating composition pressed into the mold is leveled with a leveling plate to accomplish molding. The base material, the mold plate and a receiving plate for receiving them (such as a belt of a belt conveyer) are passed as a unit between the magnet provided under the roll. The heat-generating composition is attracted on the base material through the mold with the magnet, and simultaneously, the surface of the heat-generating composition is leveled with the leveling plate along the mold to accomplish molding. Thereafter, the heat-generating composition inside the mold is transferred to the base material with the magnet. The magnet may be any one that has magnetism, and examples thereof include a permanent magnet and an electromagnet.

It is also possible that the mixing apparatus is simplified to a rotation bridge preventing apparatus, and a bridge caused upon supplying the heat-generating composition provided to the head to the mold is prevented.

In the second step, the heat-generating composition may be laminated on one location or two or more locations in the width direction on the upper surface of the base material, or may be laminated in a staggered form in the longitudinal direction of the base material.

In the third step, at least one selected from iron powder, a carbon component, ceramic powder radiating a far infrared ray, a fibrous material radiating a far infrared ray, a pyroelectric substance, a negative ion generating substance, an organic silicon compound, a water absorbing agent, a binder, a thickener, an excipient, a coagulating agent, a soluble adhesive material, a water absorbing polymer and a mesh polymer is laminated or diffused on the molded heat-generating composition, the base material or the laying material.

In the third step, at least one selected from iron powder, a carbon component, ceramic powder radiating a far infrared ray, a fibrous material radiating a far infrared ray, a pyroelectric substance, a negative ion generating substance, an organic silicon compound, a water absorbing agent, a binder, a thickener, an excipient, a coagulating agent, a soluble adhesive material, a water absorbing polymer and a mesh polymer is laminated or diffused on at least one prescribed region on the heat-generating composition laminated on the base material or the covering material in the form of a film or sheet.

In the third step A, a mesh polymer is provided on at least one, or at least a part selected from the base material, the covering material and the heat-generating composition thus laminated. This is carried out by an ordinary working technique, such as melt-blowing, printing, coating. According thereto, the laminated body of the heat-generating composition of the invention can be further firmly fixed on the base material and/or the laying material and/or the covering material. Furthermore, in the case where the polymer has adhesiveness, the base material and/or the laying material and/or the heat-generating composition and/or the covering material are adhered through the adhesiveness.

In the third step B, at least one selected form iron powder, a carbon component, ceramic powder radiating a far infrared ray, a fibrous material radiating a far infrared ray, a pyroelectric substance, a negative ion generating substance, an organic silicon compound, a water absorbing agent, a binder, a thickener, an excipient, a coagulating agent, a soluble adhesive material and a water absorbing polymer is laminated or diffused on the base material, the laying material or the covering material.

In the third step C, at least one of irradiation of a (far) infrared ray, irradiation of laser, irradiation of microwave, heating, air blasting and warm air blasting is carried out on the surface of the heat-generating composition thus laminated in an atmosphere containing oxygen, such as air or an oxygen-free atmosphere, so as to carry out dehydration, oxidation or the like.

In the fourth step, the laying material or the covering material in a film or sheet form is over laid to cover the laminated body of the heat-generating composition of the invention.

The fourth step A is a step of sealing at an outer periphery of the laminated body of the heat-generating composition by adhesion. The laying material and the covering material used herein are the same as those described for the heat-generating body of the invention. In this case, it is preferred that the base material and/or the laying material and/or the covering material are sealed by adhesion, heat adhesion or heat fusion at a periphery of the laminated body of the heat-generating composition. At least one or one of, or a part selected from the base material, the laying material and the covering material has air permeability or water permeability.

The heat-generating body for warming foot is inserted between two films or sheets, and simultaneously with the insertion, or after the insertion, and before punching the two films or sheets into a shape larger than the heat-generating body for warming foot, simultaneously with punching, or after punching, the two films or sheets are sealed at a periphery of the heat-generating body for warming foot.

After a time when the heat-generating body of a long form has been formed, the two films or sheets are sealed at a periphery of the heat-generating body for warming foot before punching the heat-generating body of a long form, simultaneously with punching the heat-generating body of a long form, or after punching the heat-generating body of a long form.

The extended parts are sealed, i.e., the two films or sheets are sealed by adhesion, heat adhesion or heat fusion at a periphery of the heat-generating body for warming foot.

Examples of the two films or sheets include those having air nonpermeability and those having air permeability. Examples thereof include those having adhesiveness and those having heat fusing property or heat adhesion property.

Examples of the film or sheet having adhesiveness include a base film or a base sheet having an air permeable adhesive layer on the whole surface thereof with a hot-melt adhesive agent, and that having air permeable or air nonpermeable adhesive layer partly on the whole surface thereof, and the base film or the base sheet may have or may not have heat adhesion property or heat fusing property by itself.

In the fifth step, the shape of the laminated body of the heat-generating composition is adjusted by compression, planarization or the like of the laminated body with a press roll or the like. That is, a desired pressure is applied to the laminated body of the heat-generating composition with a press roll or the like to adjust the shape, whereby the shape maintenance property is improved.

In particular, the method for making the heat-generating material into a sheet is not particularly limited, as far as it is a method that can make the heat-generating material into a sheet, such as a method using a rolling device of a single stage press roll, where rolling carried out once or plural times repeatedly with a single stage press roll, a method using a rolling device of a multistage press roll, where rolling is carried out plural times by one rolling operation with a multistage press roll.

In the case where the heat-generating composition cannot be formed into a sheet by only one rolling operation due to the composition thereof in this case, or in the case where the heat-generating sheet is required to change the thickness or to have a high density, the pressing operation may be carried out plural times, on which the pressure may be increased stepwise.

It is possible that pressing is carried out with the pressing roll to adhere by pressing the heat-generating material to form into a sheet form for a foot, and the heat-generating sheet is wound into a roll form to improve the storage stability, the carrying property, workability and the like, and in this case, it is possible that compression of the heat-generating sheet for a foot with the pressing roll and the winding are repeated plural times, so as to adjust the density and the air inflow property of the heat-generating sheet for a foot.

In the sixth step, dehydration, such as filtration, aspiration dehydration, centrifuge dehydration, compression dehydration with a pressing roll or the like, is carried out. In some cases, removal of water by evaporation or the like may be carried out by heating, blowing hot air or cold air, or aspiration at this time or thereafter.

The production process may be carried out in an inert gas atmosphere, such as nitrogen, argon, for preventing the iron powder from oxidation under contact with oxygen in the air.

In the seventh step, the laminated body is punched into a prescribed shape of a foot. The step of punching into a prescribed shape of a foot may be carried out by standing the laminated body still, and in this case, plural pieces of the laminated body arranged in the machine direction of the laminated body and the width direction perpendicular thereto may be simultaneously punched to form a large number of the heat-generating bodies at the same time, whereby the cost can be reduced as a result.

In this method is described before, for example, in the case where the base material in the form of a roll film or roll sheet is conveyed at a rate of from 30 to 200 m/min, on which the heat-generating composition is laminated, and then the covering material is overlaid on the heat-generating composition by guiding the covering material in the form of a roll film or roll sheet thereon by the roll, whereby the laminated body is obtained, the laminated body can be punched into an arbitrary shape by using a roll press or the like under conveying the laminated body at the conveying speed on production thereof, such as from 30 to 200 m/min, whereby the heat-generating bodies of the invention can be continuously obtained. It is needless to say that it is possible that the laminated body is once wound into a roll form, and the roll is punched by intermittently feeding.

At this time, it is possible that pressing is carried out with a pressing roll to adhere by pressing the heat-generating material on the base material constituting the packing material to laminate the heat-generating sheet on the base material, and the laminated sheet is wound into a roll form to improve the storage stability, the carrying property and the workability, and in this case, it is possible that the compression of the laminated sheet with the pressing roll and the winding are repeated plural times, so as to improve the adhesion property between the base material and the heat-generating sheet and to adjust the density and the air inflow property of the heat-generating sheet depending on necessity.

Subsequently, the heat-generating sheet is cut into prescribed size and shape with a roll cutter or the like corresponding to purposes and sealed in an air permeable packing material, and it is further sealed in an air nonpermeable packing material to prevent from contacting with the air, followed by subjecting to distribution.

In this case, cost reduction of a larger extent can be attained in such a manner that the laminated body is punched at one location or two or more continuous location in the width direction, and is continuously punched at plural locations arranged in a staggered manner along the longitudinal direction of the laminated body, so as to produce a larger number of the heat-generating bodies of the invention in a short period of time.

The laminated body is punched into such a shape that covers an arbitrary region of a foot corresponding to the purposes of the resulting heat-generating body for warming foot. That is, the laminated body obtained in the third method of the invention is punched into an arbitrary shape of a foot, so as to produce the heat-generating body of the invention.

The step of punching the laminated body of the third step in to a prescribed shape may be carried out by standing the laminated body still, and in this case, plural pieces of the laminated body arranged in the machine direction of the laminated body and the width direction perpendicular thereto may be simultaneously punched to form a large number of the heat-generating bodies at the same time, whereby the cost can be reduced as a result.

In this method, however, as described above in the case where the base material in the form of a roll film or roll sheet is conveyed, for example, at a rate of from 160 to 200 m/min, on which the non-viscous heat-generating composition having excessive water is laminated, and then the covering material is overlaid on the non-viscous heat-generating composition having excessive water by guiding the covering material in the form of a roll film or roll sheet thereon by the roll, whereby the heat generating sheet of the laminated body is obtained, because the laminated body stands still in the punching step, it is necessary that the laminated body is once wound into a roll form and then the roll is punched by intermittently feeding, whereby the production process becomes complicated, the production time is prolonged, and there is a limitation in improving working efficiency due to the punching operation intermittently carried out.

Therefore, in the third step of the invention, in order to simplify the production process and to shorten the production time, it is preferred that the laminated body is punched into an arbitrary shape of a foot by using a roll press under conveying the laminated body at the conveying speed on production thereof, such as from 160 to 200 m/min, so as to obtain the heat-generating body for warming foot.

In the case where a roll press is used, because the laminated body can be continuously punched, and the production and the punching of the laminated body can be carried out by a consistent and continuous operation, a large number of heat-generating bodies for warming foot can be completed in a short period of time, and as a result, the cost can be reduced by a large extent compared with the method of standing still and punching the laminated body.

In this case, cost reduction of a further larger extent can be attained by completing a further larger number of heat-generating bodies for warming foot in a short period of time in such a manner that plural laminated bodies are simultaneously and continuously punched by arranging in the width direction perpendicular to the machine direction of the laminated body or by arranging in a staggered manner along the machine direction and the width direction of the laminated body.

In the punching of the laminated body, it is punched into such a shape that covers an arbitrary part of a foot. That is, it is punched in such a shape that the resulting laminated body covers an arbitrary part of a foot, and the heat-generating body for warming foot thus punched is not particularly limited, for example, such a shape that covers a part or a whole of a bottom or an in step of a foot, and the like, and may have an arbitrary shape.

The heat-generating body for warming foot is inserted between two films or sheets, and simultaneously with the insertion, or after the insertion, the two films or sheets are punched into a larger shape than the heat-generating body for warming foot.

The punching may be carried out by standing still the heat-generating body for warming foot intervening between the two films or sheets, i.e., the long sheet heat-generating body, and in this case, plural pieces of the long sheet heat-generating body arranged in the machine direction of the laminated body and the width direction perpendicular thereto may be simultaneously punched to form a large number of the heat-generating bodies for warming foot at the same time, whereby the cost can be reduced as a result.

In this case, the operation of punching into a larger shape than the heat-generating body for warming foot means is not particularly limited as far as it is such a shape that is larger than the size of the heat-generating body for warming foot, and in particular, it is preferably a shape similar or substantially similar to the shape of the heat-generating body for warming foot, and is larger than that shape by extending from the entire periphery in about from several millimeter to 20 mm.

In the eighth step, the heat-generating body for warming foot is inserted between two films or sheets, and simultaneously with the insertion, or after the insertion, the two films or sheets are sealed at a periphery of the heat-generating body to a size exceeding the size of the heat-generating body, and simultaneously with the sealing, or after the sealing, it is punched.

EXAMPLE

The heat-generating body of the invention will be described in more detail with reference to examples, but the invention is not limited thereto.

Example 1

A heat-generating body for warming foot shown in FIG. 1 is a heat-generating body for warming foot 1 having an entire foot shape having a heat-generating composition sandwiched by a base material and a covering material, and the base material and the covering material are sealed 6 with a width of 10 mm outside the periphery of the heat-generating composition 1A.

Figure 2:
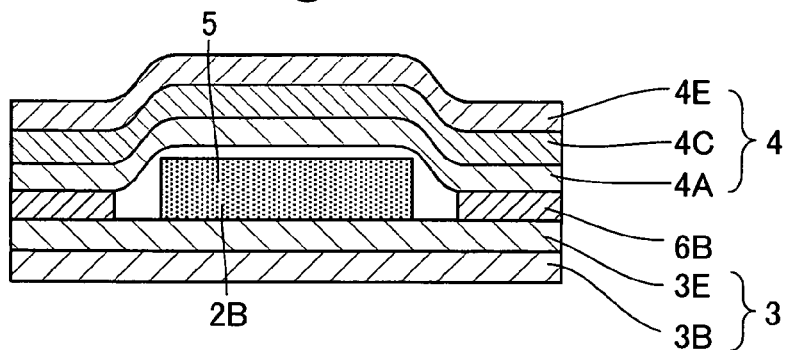
FIG. 2 is a cross sectional view on line X-Y of the same figure.

A schematic cross sectional view thereof is shown in FIG. 2. As the base material 3, a corrugated fiberboard liner 3E having a thickness of 100 µm and a layer having a thickness of 50 µm and having air nonpermeability and water nonpermeability formed with polyethylene 3B produced with a metallocene catalyst are provided. On the base material 3, a non-viscous heat-generating composition having excessive water 2B on the corrugated fiberboard liner 3E is molded through a mold in direct contact therewith.

The covering material 4 is formed by laminating a porous film 4C having a thickness of about 50 µm on a corrugated fiberboard liner 4A having a thickness of 50 µm, and the moisture permeation degree thereof is 1,000 g/m$^2$·24 hr. A PP nonwoven fabric having a basis weight of about 80 g/m$^2$ 4E is laminated thereon, and the moisture permeation degree thereof is 1,000 g/m$^2$·24 hr. In the covering material 4, the covering material 4 is laminated in such a manner that the non-viscous heat-generating composition having excessive water 2B is in direct contact with the corrugated fiberboard liner 4A.

The non-viscous heat-generating composition having excessive water 2B was prepared by mixing 0.3 part by weight of a water absorbing polymer (KI-gel 201K, produced by Kuraray Co., Ltd.), 3.0 parts by weight of wood powder, 8.0 parts by weight of activated carbon (SA-Super, produced by Norid, Inc), 4.0 parts by weight of sodium chloride, 0.15 part by weight of calcium hydroxide and 50 parts by weight of water with 100 parts by weight of iron powder (DKP, produced by Dowa Teppun Co., Ltd.). The non-viscous heat-generating composition having excessive water 2B had an incremental degree of viscosity of 500 cP and a water mobility value of 12.

Therefore, the non-viscous heat-generating composition having excessive water 2B contains an excessive water content. The excessive water content prevent the iron powder from contacting with air as a barrier layer, and as a result, it was found that substantially no heat-generating reaction occurred.

Upon molding the non-viscous heat-generating composition having excessive water 2B on the base material 3 by mold-through molding by using a mold having a thickness of 1,500 µm, the excessive water content in the non-viscous heat-generating composition having excessive water 2B is started to be absorbed by the water absorbing corrugated fiberboard liner 3E in the base material 3, and after overlaying the covering material 4, also absorbed by the corrugated fiberboard liner 4A of the covering material 4, and thereafter, the mixing ratio of water in the heat-generating composition becomes such a state that is optimum for causing the prescribed heat generation temperature.

After lapsing at least two days from sealing the heat-generating body for warming foot in an air nonpermeable bag, the excessive water content in the non-viscous heat-generating composition having excessive water is absorbed by the water absorbing rayon nonwoven fabric in the base material and the water absorbing corrugated fiberboard liner in the covering material, and thus it becomes such a mixing ratio of water content that is suitable for obtaining the prescribed heat generation temperature. Therefore, the quality of the heat-generating composition is not deteriorated until it is in contact with air by breaking the air nonpermeable bag to maintain the quality of the heat-generating composition to high quality, and when the heat-generating body for warming foot is taken out by breaking the air nonpermeable bag, the heat-generating reaction is immediately started to increase the temperature to a prescribed heat generation temperature.

The heat-generating body for warming foot was sealed in an air nonpermeable bag and allowed to stand for 2 days, and then the heat-generating body for warming foot was taken out by breaking the air nonpermeable bag, followed by using by placing in a leather shoe. Warm feeling was obtained after 30 to 60 seconds, and excellent warming effect was obtained for 6 hours or more.

Upon application of the heat-generating body for warming foot, it becomes flexible in total since the heat-generating body is formed to have an ultrathin form, and as a result, it provides soft feeling to the foot, it is easily deformed along the curved part of the foot, it is fit to the irregularity on the bottom of the foot, it is deformed by well following the movement of the bottom of the foot, and it is good in adhesion to the applied part. Furthermore, the heat-generating body for warming foot is not released from the applied part during use, but excellent warming effect is obtained, and thus it is confirmed that the foot can be effectively warmed from the bottom.

That is, upon using the same, the region over the whole of the foot can be effectively warmed owing to the heat-generating body for warming foot having an entire foot shape.

Furthermore, upon using the same, the heat-generating composition does not migrate, whereby the distribution of the heat generation temperature is uniform, and thus low temperature ambustion is not caused to provide high safety.

The non-viscous heat-generating composition having excessive water can be laminated on the base material by using such a technique as mold-through molding, printing or coating owing to the high flowability, and as a result, it can be accurately laminated at a high speed on the prescribed region with a uniform thickness in comparison to the case where a conventional powder heat-generating composition having no flowability is simply dropped on a base material.

Figure 3:
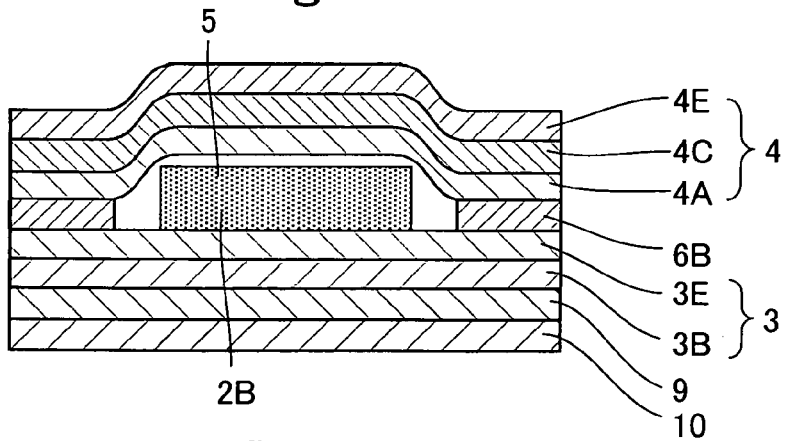
FIG. 3 is a cross sectional view of another example of a heat-generating body of the invention.

FIG. 3 is an example where the liner paper of the base material 3 is replaced with kraft paper, and an antislipping layer is further provided. There is nothing to say that it is possible that the antislipping layer or the like is covered with a protective layer, such as releasing paper or the like, to protect the antislipping layer.

Example 2

Figure 4:
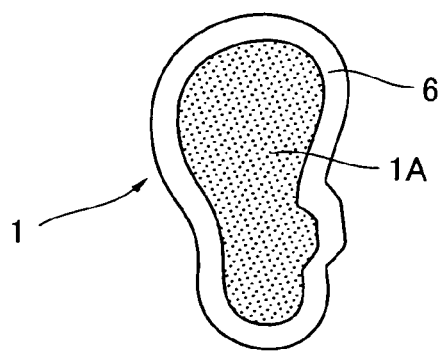
FIG. 4 is a plane view of another example of a heat-generating body of the invention.

In the heat-generating body for warming foot 1 shown in the plane view of FIG. 4, a non-viscous heat-generating composition having excessive water 1A is molded into a form obtained by adding an arch and a part extending from the arch to the shape in Example 1 by mold-through molding, and the part other than the non-viscous heat-generating composition having excessive water is sealed 6 by adhesion as in Example 1.

The base material, which is different from Example 1, rayon-polyester mixed nonwoven fabrics having a thickness of 140 μm and a rayon fiber content of 60% by weight are laminated on both surfaces of a polyethylene film having water absorbing property and a thickness of 80 μm instead of the paper.

As the covering material, the non-viscous heat-generating composition having excessive water and the adhesive agent layer, those that are the same as in Example 1 are used.

Example 3

Figure 5:
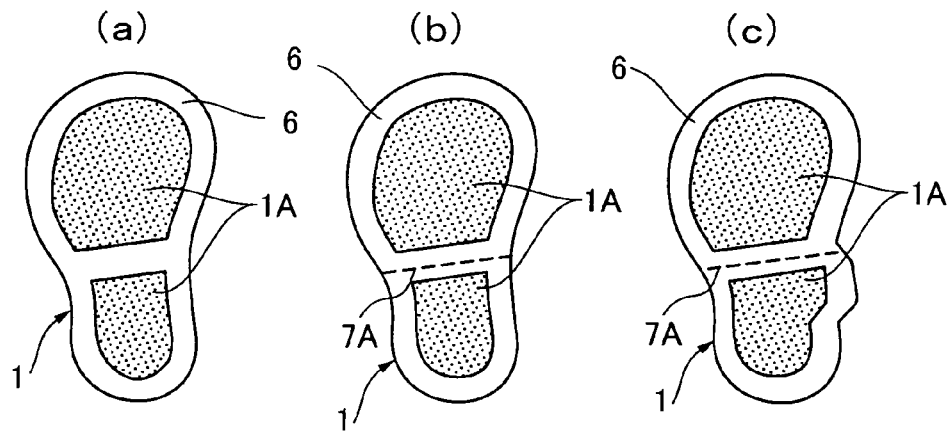
FIGS. 5(a) to 5(c) are plane views of other examples of a heat-generating body of the invention.

In the heat-generating body for warming foot shown in the plane view of FIG. 5(a), a heat-generating composition 1A is formed by mold-through molding on two regions at the substantially central position of the shape as in Example 1, and the part other than the non-viscous heat-generating composition having excessive water 1A is sealed by cohesion 6. On the substantially central position where the heat-generating composition 1 is not laminated, the heat-generating body for warming foot can be folded and thus can be made compact. Since the surface area can be reduced upon storing, deterioration of the heat-generating composition due to scattering of water can be reduced. (b) is such a product that has a perforated line 7A on the region having no heat-generating composition to facilitate folding. (c) is a such a product that is added with a part extending from the arch.

Figure 6:
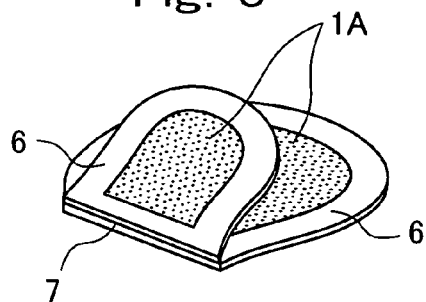
FIG. 6 is a perspective view of another example of a heat-generating body of the invention.

The heat-generating body for warming foot 1 shown in the plane view of FIG. 6 shows a perspective view of the case where the heat-generating body for warming foot 1 of FIG. 5(b) is folded into two.

Example 4

Figure 7:
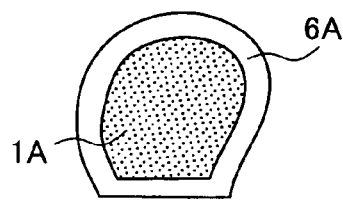
FIG. 7 is a cross sectional view of another example of a heat-generating body of the invention.
Figure 8:
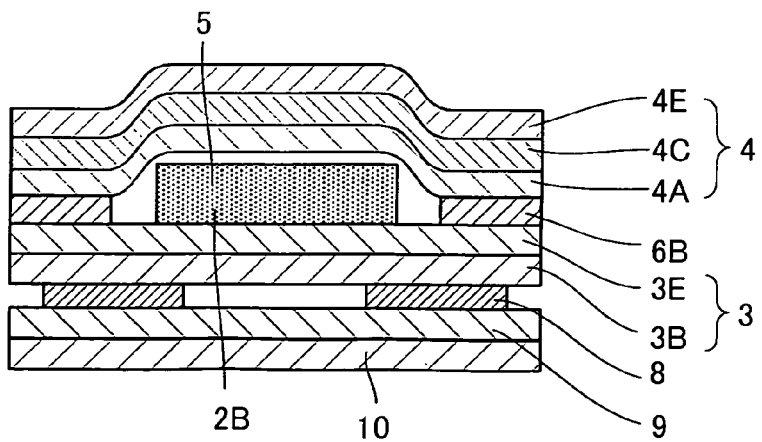
FIG. 8 is a plane view of another example of a heat-generating body of the invention.

The heat-generating body for warming foot 1 shown in the plane view of FIG. 7 is an example of a heat-generating body for warming foot 1 warming a region in a half-foot shape on the digit side. As a covering material, a propylene nonwoven fabric having a basis weight of 80 g/m² is laminated on one surface of a porous film having a thickness of 40 μm, and kraft paper is laminated on the other surface thereof through an air permeable hot-melt adhesive layer to form an air permeable covering material. The moisture permeability thereof was 2,500 g/m²·24 hr. As a base material, a material obtained by laminating a propylene nonwoven fabric and a polyethylene film is partly provided with an adhesive agent layer formed with an acrylic adhesive agent on the side of the polyethylene film, and releasing paper is provided further thereon. A formed article of the heat-generating composition is formed with a laminated product of the heat-generating composition and a water absorbing polymer. FIG. 8 shows across sectional schematic view thereof.

As similar to Example 1, the heat-generating body for warming foot was sealed in an air nonpermeable bag and allowed to stand for 10 day. The heat-generating body for warming foot was then taken out by breaking the air nonpermeable bag and was used by applying directly to a part of a bottom of a foot extending from digits to roots thereof toward pads with the adhesive agent layer, and thus excellent warming effect was obtained for 6 hours or more.

Upon application of the heat-generating body for warming foot, it becomes flexible in total since the heat-generating body is formed to have an ultrathin form, and as a result, it provides soft feeling to the foot, it is easily deformed along the curved part of the foot, it is fit to the irregularity on the bottom of the digits of the foot, it is deformed by well following the movement of the bottom of the foot, and it is good in adhesion to the applied part. Furthermore, the heat-generating body for warming foot is not released from the applied part during use, but excellent warming effect is obtained, and thus it is confirmed that the digits of the foot can be effectively warmed from the bottom.

That is, upon using the same, the region of the foot from the toe to the pads on the root of the digits can be effectively warmed from the bottom owing to the fact that the adhesive agent layer of the heat-generating body for warming foot can be directly attached to the bottom of the foot.

Furthermore, upon using the same, the heat-generating composition 2B does not migrate, whereby the distribution of the heat generation temperature is uniform, and thus low temperature ambustion is not caused to attain warming comfortably with high safety.

Example 5

Figure 9:
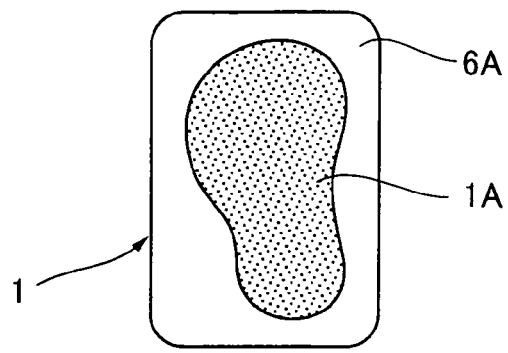
FIG. 9 is a plane view of another example of a heat-generating body of the invention.

In the heat-generating body for warming foot 1 shown in FIG. 9, a heat-generating composition 1A is formed into a foot shape, and a base material 6A and a covering material 6A are formed into a rectangular shape.

In this example, the covering material 6A is formed by laminating a polypropylene nonwoven fabric (basis weight: 30 g/m²) and a polyethylene porous film (thickness: 40 μm) as outer layers with a corrugated fiberboard liner (basis weight: 200 g/m², water absorbing amount: 114 g/m²) as an inner layer through a hot-melt adhesive agent formed by melt-blowing, and the basis weight of the hot-melt adhesive agent is 5 g/m² between the nonwoven fabric and the porous film and is 30 g/m² between the porous film and the corrugated fiberboard liner. The moisture permeability of the covering material is 3,000 g/m²·24 hr. The base material is formed by laminating an extruded laminate of polyethylene formed by using a metallocene catalyst as an outer layer with a corrugated fiberboard liner (basis weight: 200 g/m², water absorbing amount: 114 g/m²) as an inner layer through a hot-melt adhesive agent formed by melt-blowing, and the basis weight of the hot-melt cohesive agent is 30 g/m².

The heat-generating body for warming foot was sealed in an air nonpermeable bag and allowed to stand for 30 day. The heat-generating body for warming foot was then taken out by breaking the air nonpermeable bag and was used by laying on a shoe sole, and thus excellent warming effect was obtained for 7 hours.

Example 6

Figure 10:
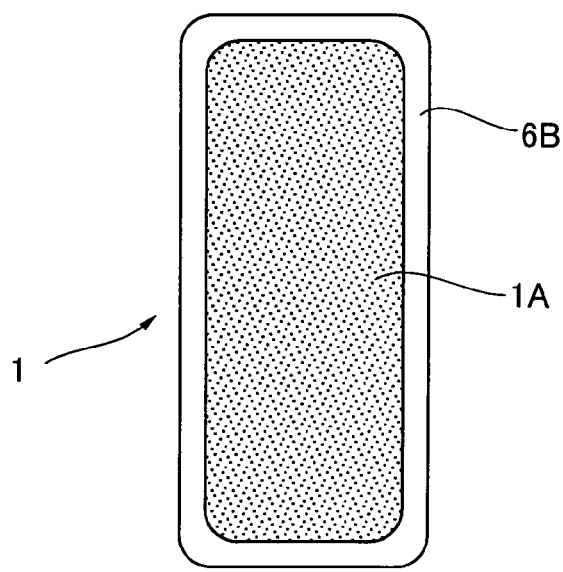
FIG. 10 is a plane view of another example of a heat-generating body of the invention.

In the heat-generating body for warming foot 1 shown in the plane view of FIG. 10, a heat-generating composition 1A, a base material 6B and a covering material 6B are formed into a rectangular shape, and four corners thereof are rounded.

Example 7

Figure 11:
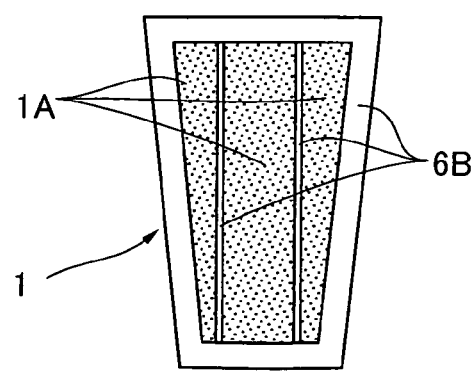
FIG. 11 is a plane view of another example of a heat-generating body of the invention.

In the heat-generating body for warming foot shown in the plane view of FIG. 11, a heat-generating composition 1A is formed into an inverse trapezoidal form by mold-through forming, and the part other than the non-viscous heat-generating composition having excessive water is sealed by pressing with adhesion. The heat-generating composition is divided into three (1A, 1A and 1A) in the longitudinal direction.

It is a low cost and inexpensive heat-generating body for warming foot formed in such a manner that after sealing a laminated body of the heat-generating composition, four corners of an outer periphery of the laminated body of the heat-generating composition at a position by 10 mm from the periphery thereof are not rounded.

Example 8

Figure 12:
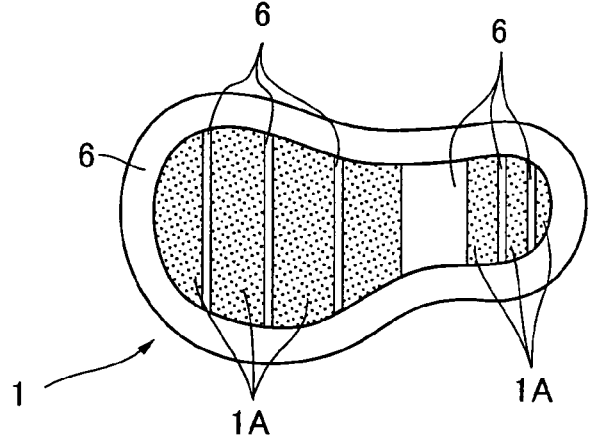
FIG. 12 is a plane view of another example of a heat-generating body of the invention.

The heat-generating body for warming foot 1 shown in the plane view of FIG. 12 is such a heat-generating body for warming foot in that a heat-generating composition 1A is divided in the longitudinal direction and the direction perpendicular thereto into plural parts.

Example 9

Figure 13:
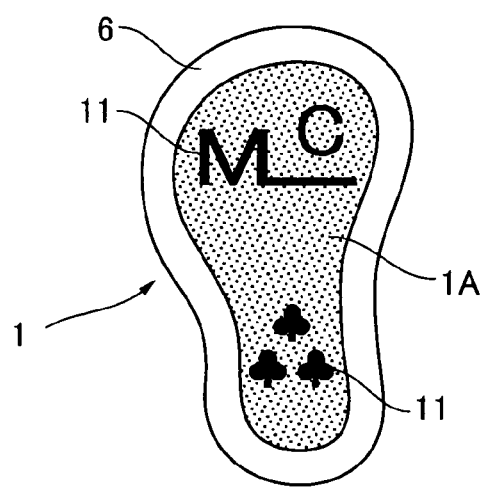
FIG. 13 is a plane view of another example of a heat-generating body of the invention.

The heat-generating body for warming foot 1 shown in the plane view of FIG. 13 is an example having an entire foot shape and provided with a design containing characters and patterns on one surface.

Example 10

Figure 14:
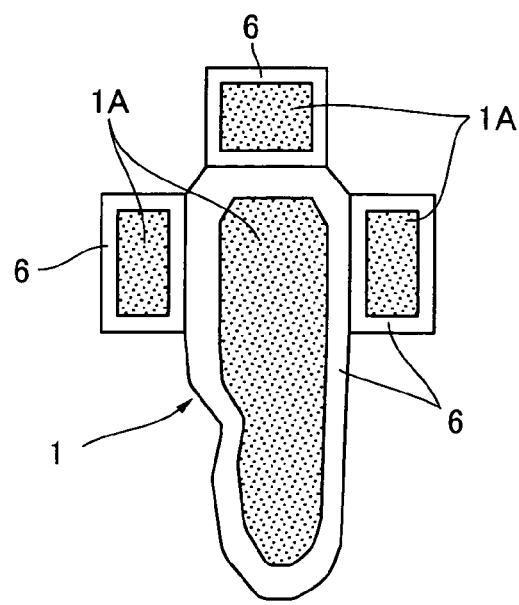
FIG. 14 is a plane view of another example of a heat-generating body of the invention.

In the heat-generating body for warming foot 1 shown in FIG. 14, a bulge part covering from a toe part to a top edge surface of the toe of the foot shape and a bulge part covering from the toe to an in step are provided, and a non-viscous heat-generating composition having excessive water 1A are arranged on the respective parts.

According to the heat-generating body for warming foot 1, the toe part can be warmed from three faces, i.e., the bottom of the foot, the side of the toe and the in step side, by extremely easily folding the bulge parts from the toe to the in step.

While not shown in the figure, it is possible that fixing straps are connected to both side ends of the toe side of the foot shape part A, and adhesive layers are laminated on tip end parts of the fixing straps.

Example 11

Figure 15:
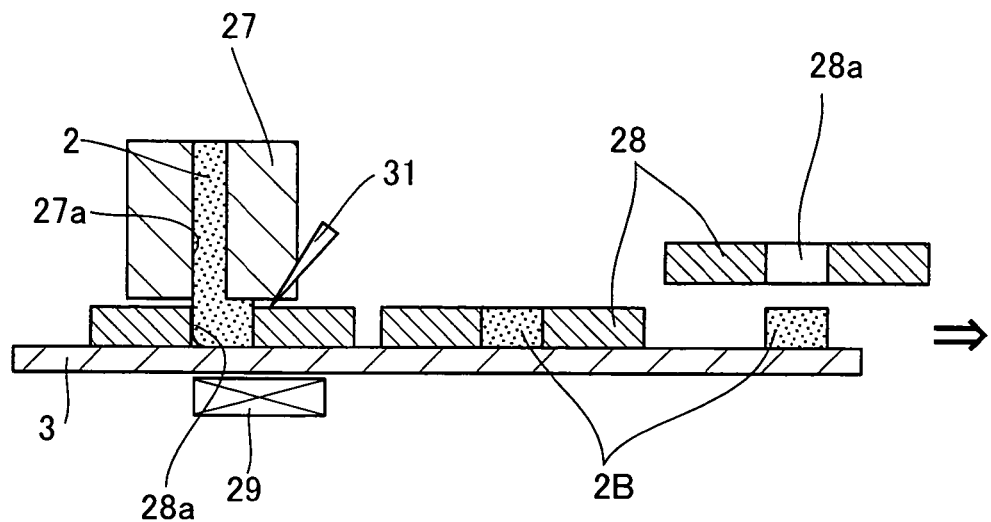
FIG. 15 is a schematic view of mold-through forming according to another example of the invention.

FIG. 15 shows an example of a mold-through molding method by using a leveling plate 31. That is, a base material 3 in a form of a roll film having a width of 130 mm is horizontally conveyed at a prescribed speed between a dice 27 upward and a magnet 29 downward, which are arranged in such a manner that, accommodating with a mold 28 for molding having a thickness of 1 mm and having a vacancy of a desired shape at a center of the mold, the dice 27 is arranged on the upper surface thereof, and the magnet 29 is arranged on the lower surface thereof. The non-viscous heat-generating composition having excessive water 2B is fed to the mold vacancy 28*a* from the upper surface of the mold 28 through a hole 27*a* of the dice 27. The heat-generating composition 2B is leveled to the same surface of the mold 28 with the leveling plate 31 placed ahead in the conveying direction and simultaneously charged in the mold vacancy 28*a*, so as to be molded to a desired shape with a thickness of 1 mm on the base material 3. Thereafter, the mold 28 is released to obtain a mold article 2B laminated on the base material 3.

Figure 16:
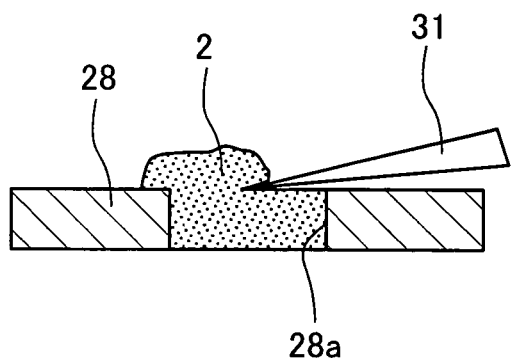
FIG. 16 is a schematic view of forming using a leveling plate according to another example of the invention.
Figure 17:
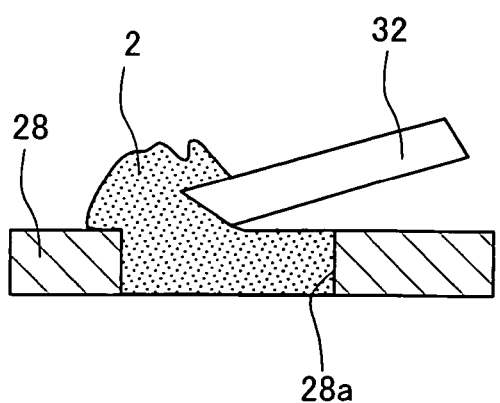
FIG. 17 is a schematic view of forming using a pressing and leveling plate according to another example of the invention.

While not shown in the figure, a cohesive polymer of a styrene-isoprene-styrene block copolymer (SIS) series is provided in a mesh form on the molded article by a melt blowing method, a covering material is overlaid thereon, and the periphery of the molded article region is sealed by heat sealing, followed by cutting into a desired shape, so as to obtain a heat-generating body having a desire shape. Furthermore, the heat-generating body of the invention thus cut is fed to a packing step to be sealed in an outer bag having airtightness. The same molding can be carried out by using a pressing and leveling plate instead of the leveling plate 31. FIG. 16 shows the pressing and leveling plate 31, and FIG. 17 shows the pressing and leveling plate 32. The tip end part of the pressing and leveling plate may be subjected to any type of deformation, such as trimming to provide roundness, as far as the pressing and leveling function is maintained.

Example 12

Figure 18:
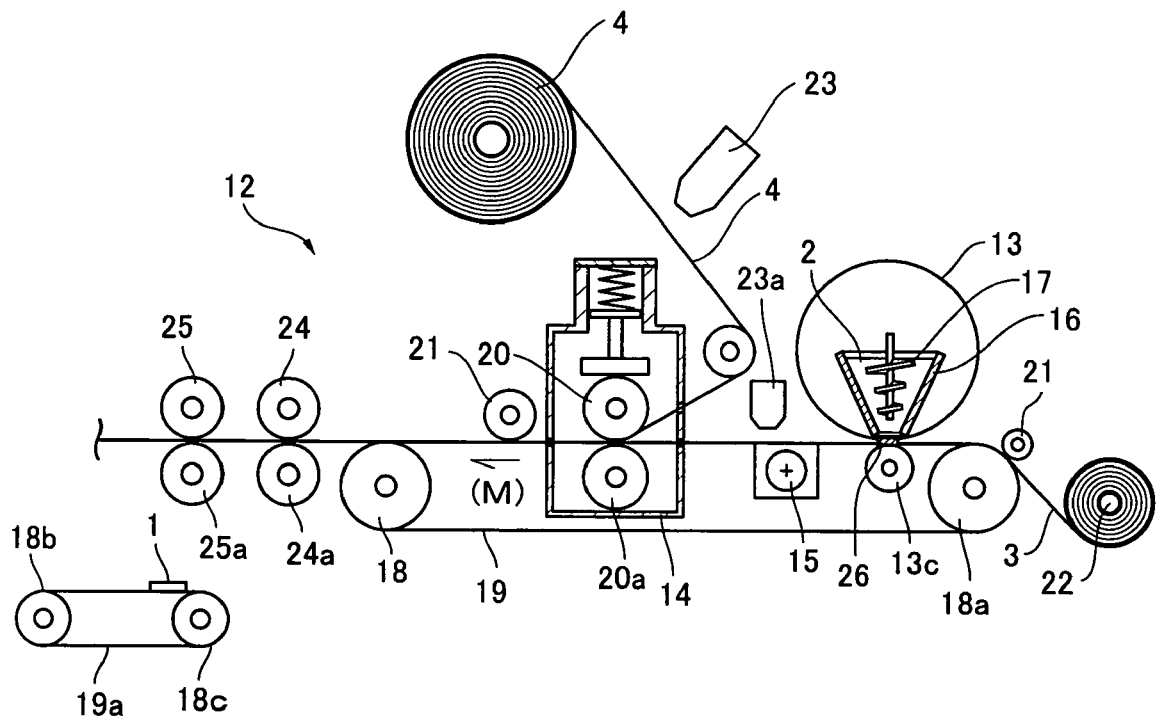
FIG. 18 is an explanatory view showing an apparatus for producing a heat-generating body of the invention.

FIG. 18 shows a production apparatus 12 for preferably producing a heat-generating body according to the invention. As shown in the figure, the production apparatus 12 is constituted with a drum molding device 12 for molding the non-viscous heat-generating composition having excessive water, a rolling device 14 for adjusting by rolling the thickness of the heat-generating composition in a squamous form or a sheet form obtained in the drum molding device 12, die rolls 24 and 24*a* for sealing, and die cut rolls 25 and 25*a* for cutting. In this case, the non-viscous heat-generating composition having excessive water used in Example 1 was used as the non-viscous heat-generating composition having excessive water.

The drum molding device 12 is equipped with a screw 17 inside a hopper 16 positioned on the upstream (upper right in the figure) of the production apparatus 12.

The rolling device 14 has press rolls 20 and 20*a* provided in the course of conveying direction of a belt conveyer 19 made of stainless steel positioned under the molding device 12, so as to sandwich the belt conveyer 19 vertically. A driving device 15 is a driving power source for the belt conveyer 19 and the press rolls 20 and 20*a*. Furthermore, a tension roller 18, a base material pressing roll 21 is provided on one side of the belt conveyer 19, ahead of them die rolls 24 and 24*a* for sealing and the die cut rolls 25 and 25*a* are provided.

The numerals 18 and 18*a* in the figure denote supporting rollers for the belt conveyer 19. While not shown in the figure, the belt conveyer 19 and the press rolls 20 and 20*a* can be driven inversely through operation of a switch after releasing the die rolls 24 and 24*a* for sealing and the die cut rolls 25 and 25*a* as not shown in the Fig.

The process for producing a heat-generating body in a sheet form (heat-generating sheet) will be described with reference to FIG. 18.

The base material 3 wound in a roll form is fed at 50 m/min, and the heat-generating composition 2 described in Example 1 is placed in the hopper 16. Upon rotating the screw 17, the composition 2 is molded from the hopper 16 to the belt conveyer 19 through the drum molding device 13 as a molded article 26 in a squamous form or a sheet form on a center part of a water absorbing film as the base material 3 by mold-through molding to a size of 110 mm×70 mm with every interval of 20 mm. Furthermore, the heat-generating composition 26 thus molded is covered with a covering material 4 fed from the covering material in a roll form 4, which is formed with a porous film having coated on the whole surface thereof a hot-melt adhesive agent with a melt blowing machine 23 at a temperature of 160° C. to 5 g/m$^2$, in the course of conveying in the direction (M) on the belt conveyer 19, that is, on the base material 3 and laminated heat-generating composition 26 so as to make in contact with the hot melt cohesive agent, and then it is rolled with the press rolls 20 and 20a and further sealed at a periphery of the base material 3 and the covering material 4 with a die rolls 24 and 24a to a size of 130 mm×80 mm, followed by cutting with the die cut rolls 25 and 25a, so as to obtain a heat-generating body 1. The heat-generating body 1 shows the heat-generating body 1 in a sheet form thus cut into a sheet form. It is possible that the melt blowing machine 23 is changed to a melt blowing machine 23a, so that the hot melt adhesive agent layer is made in contact with the laminated product of the heat-generating composition and/or the base material 3.

In this case, the base material 3 is formed with a five-layer film with stretch property having a width of 130 mm. That is, a polyester spunless nonwoven fabric having a basis weight of 40 g/m$^2$ is laminated on a polyester releasing film 6 having a thickness of 38 μm with a hot melt cohesive agent layer having a basis weight of 150 g/m$^2$ intervening there between, and a water absorbing film formed by containing a water absorbing polymer in an amount of 25 g/m$^2$ in a polyester spunless nonwoven fabric having a basis weight of 30 g/m$^2$ is adhered under heat on the side of the polyester spunless nonwoven fabric of the three-layer film with a polyethylene film (polymer formed with a metallocene catalyst) with rubber elasticity having a thickness of 30 μm intervening there between, so as to provide the five-layer film.

On the other hand, the covering material 4 is formed with a three-layer film with stretch property having a width of 130 mm. That is, a hot melt cohesive agent layer having a basis weight of 5 g/m$^2$ is formed on a porous film having a basis weight of 50 g/m$^2$ at a temperature of 160° C. with a melt blowing machine 20, and a polyester spunless nonwoven fabric having a basis weight of 30 g/m$^2$ is laminated on the hot melt cohesive agent layer to form the three-layer film.

The covering material 4 has a moisture permeability of 410 g/m$^2$·24 hr.

As the heat-generating composition, that such a product was used that was prepared in such a manner that 4.5 parts by weight of sodium chloride (NaCl), 45 parts by weight of water, 8.0 parts by weight of activated carbon, 0.3 part by weight of a water absorbing polymer, 5.0 parts by weight of wood powder (having a particle size passing 100 mesh) and 50 parts by weight of water were mixed with 100 parts by weight of iron powder (DKP, produced by Dowa Teppun Co., Ltd.).

The non-viscous heat-generating composition having excessive water had an incremental degree of viscosity of 200 cP and a water mobility value of 15.

By using the non-viscous heat-generating composition having excessive water, stable lamination of the heat-generating composition by mold-through molding on a central part of the water absorbing film in the base material 3 can be carried out, whereby the lamination region can be controlled with high accuracy, and the film thickness can be controlled to a very small thickness with uniformity. Furthermore, the heat-generating composition 2 is prevented from moving inside the bag body 1 owing to the bonding force between the water absorbing film in the base material 3 and the heat-generating composition 2. The thickness of the heat-generating composition layer 2 is made small, and thus the heat-generating body can be formed into an ultrathin form.

In this example, the water absorbing base material 3 in the form of a roll film having a width of 130 mm is horizontally conveyed at a speed of 200 mm/min, and the heat-generating composition layer is molded through the mold on the upper surface thereof at a thickness of about 1.0 mm. Immediately after the mold-through molding, a hot-melt adhesive agent is previously coated on the whole surface of the porous film of the water absorbing covering material by a melt blowing method at a temperature of 160° C. to 5 g/m$^2$, and simultaneously, the covering material 4 is overlaid thereon in such a manner that the hot-melt adhesive agent layer is in contact therewith, followed by sealing a periphery thereof with the hot-melt adhesive agent layer, so as to produce a heat-generating body in an ultrathin form having a thickness of about 0.94 mm. Such a rolling method in that the composition and the components of the heat-generating composition of the invention is formed into a heat-generating sheet having a desired thickness by rolling once using a pair of rolling means is referred to as the single stage press roll method.

It is needless to say that in the case where a heat-generating sheet having a desired thickness cannot be obtained by rolling once or in the case where change in thickness or a high density is required, the belt conveyer 16 and the press rolls 17 and 17a are driven in the invert direction before cutting with the die cut rolls, whereby the heat-generating composition 1 in a sheet form sandwiched by the base material and the covering material is conveyed, and the heat-generating composition 1 is again subjected to rolling with the press rolls 17 and 17a. Furthermore, it is also possible that the process steps are repeated to produce sheets having various densities and thickness. The heat-generating body in a sheet form thus again rolled 2 is further cut with the die cut rolls 22 and 22a.

The thus cut heat-generating body is conveyed to a packing step and sealed in an outer bag having air tightness not shown in the figure.

The excessive water content of the heat-generating composition layer is controlled with the water mobility value, and thus it is gradually absorbed by the base material 3 after molding through the mold on the base material 3, and the covering material 4 is overlaid thereon. However, the period of time from the mold-through molding of the heat-generating composition 2 on the base material 3 to the sealing in the outer bag is extremely short, and thus, there are substantially no case where the excessive water content of the heat-generating composition layer is absorbed by the base material 3 to such an extent that causes a heat-generating reaction.

Therefore, there is substantially no possibility of causing a heat-generating reaction of the heat-generating composition in the production process, and there is completely no possibility of causing loss due to the heat-generating reaction and quality deterioration of the heat-generating composition. Furthermore, there is substantially no possibility that the heat-generating composition is solidified in the process steps from the mixing of the heat-generating composition to the mold-through molding on the base material 3, whereby various kinds of problems can be prevented, such as reduction in yield due to solidification, termination of the operation, restriction in operation time, difficulty and danger in cleaning the production apparatus, frequency in cleaning the production apparatus, difficulty in processing solidified products.

After sealed in an outer bag, it was taken out by breaking the outer bag after lapsing 24 hours and was attached on the surface of a human body to subject to ordinary use. It was increased in heating temperature until about 36° C. within about from 1 to 2 minutes, and generated heat at about from 37 to 39° C. for 6 hours or more. During the use, the heat-generating composition layer 2 was not moved inside the bag 1 to provide uniform heat generation over the whole surface.

Furthermore, instead of the method carried out in Example 1, i.e., the hot melt adhesive agent is previously coated on the whole surface of the porous film of the covering material by a melt blowing method to ensure air permeability, the covering material is overlaid on the heat-generating composition 2 to make the hot melt adhesive agent layer in contact therewith, such a method may be employed in that a hot melt adhesive agent is coated to ensure air permeability by a melt blowing method on the heat-generating composition layer and the base material formed in the same manner as in Example 1, and the covering material is overlaid thereon to make the porous film side thereof in contact with the hot melt adhesive agent.

Instead of the method of coating a hot melt adhesive agent by a melt blowing method on the whole surface of the porous film of the covering material, such a method may be employed in that an isoprene adhesive agent is transferred by gravure printing on the surface periphery of the porous film of the covering material, and the base material and the covering material are sealed with the isoprene adhesive agent.

It is also possible to obtain a heat-generating body in the following manner. An acrylic adhesive agent layer having a thickness of 50 μm is formed on the whole surface of the water absorbing film of the base material by a known method. The base material wound in a roll form is conveyed, and simultaneously, the heat-generating composition is magnetically transferred by a known magnetic transferring method to the center part of the acrylic adhesive agent layer, i.e., the heat-generating composition is attached to a magnet sheet. Furthermore, the heat-generating composition is magnetically transferred to the base material with another magnet sheet at regular time intervals, and the covering material is overlaid thereon, i.e., on the base material and the heat-generating composition, in such a manner that the porous film thereof is in contact therewith. The periphery of the base material and the covering material is sealed with the acrylic adhesive agent by passing through nip rolls, and cut into a prescribed size, so as to obtain a heat-generating body.

In the case the periphery of the heat-generating body, i.e., the periphery of the base material and the covering material, is sealed by using a adhesive agent, it is possible that they are subjected to a heat treatment at 60° C. partially with a prescribed interval in a linear form, whereby the sealing of the base material and the covering material is further ensured but is difficult to be released with improved reliability.

Figure 19:
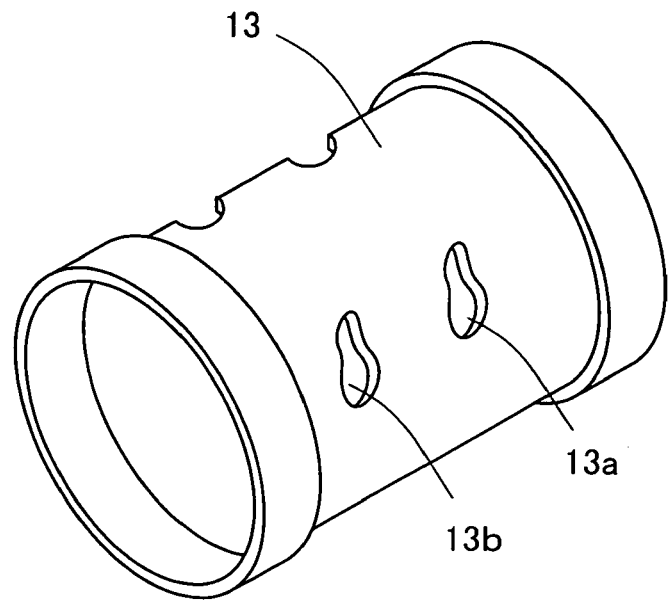
FIG. 19 is an explanatory view showing an example of a drum for forming a sole form.

FIG. 19 shows an example of a drum for forming a sole form.

INDUSTRIAL APPLICABILITY

As described in the foregoing, the heat-generating body for warming foot of the invention has the following effects.

(1) Because the shape retaining degree of the heat-generating molded article is 70 or more, and correlatively, the heat-generating body for warming foot is formed in to an ultrathin form, shape maintenance by decompression may not be carried out, and thus any film of a porous film, a perforated film and the like can be used, the range of selection of air vent holes of the air permeating part is dramatically enhanced, the heat-generating characteristics can be designed more delicately, occurrence of an abnormally high temperature point or an abnormally high temperature part due to deviation of the heat-generating composition can be certainly prevented, occurrence of low temperature ambustion can be certainly prevented, and the safety upon use is further improved, whereby more comfortable foot warming can be carried out.

(2) Because the heat-generating composition has improved liquid permeability, in the case where the water mixing ratio in the heat-generating composition is adjusted to a mixing ratio suitable for heat generation by absorbing the excessive water content with the base material or the like after molding, and then the airtight bag for storage is broken upon use, heat generation immediately proceeds, whereby the prescribed heat generation temperature is quickly obtained, and the prescribed heat generation temperature can be retained for a long period of time.

(3) Because various kinds of shapes can be produced, it has high fitness to complicated concave and convex shapes of an arbitrary part of a foot, such as a curved part, a bending part, it can be applied to an arbitrary part of a foot, such an arbitrary part of a foot that is necessarily warmed can be effectively warmed, and as a result, excellent warming effect can be obtained.

(4) Since an adhesive agent layer or an antislipping layer is formed on one of exposed surfaces of the base material or the covering material, the heat-generating body for warming foot can be easily fixed to an arbitrary part of a foot, and migration of the heat-generating body itself in a footgear can be prevented, whereby a desired part can be maintained at a suitable temperature.

(5) Because of the use of the non-viscous heat-generating composition having excessive water, the flowability is extremely high in comparison to the conventional powder heat-generating composition, and it can be continuously and accurately laminated to a uniform and very small thickness in a prescribed region by mold-through molding, printing or coating on a base material that is conveyed at a high speed, for example, more than 100 m per minute.

(6) Upon carrying out the high speed production, in order to entrain the feeding device of the base material, the laminating device of the non-viscous heat-generating composition by mold-through molding or the like, the laminating device of the covering material, the molding device, such as the punching device of the heat-generating body for warming foot for punching the resulting laminated body into such a shape that covers an arbitrary part of a foot, the packaging device for sealing the heat-generating body for warming foot into an airtight bag, and the like, it is sufficient that such an adjustment is carried out that the operation speed is entrained, whereby production by high speed continuous operation can be carried out with a simple device constitution.

(7) Scattering of powder of the heat-generating composition to environments as in the conventional art is prevented, and thus such a factory management can be attained that completely satisfies the future GMP standard on production of medical devices and medical drugs.

(8) Because the non-viscous heat-generating composition having excessive water excellent in water permeability is imparted with moldability and shape maintenance property by the surface tension of water, the heat-generating composition can be easily molded by mold-through molding using a magnet and a leveling plate, and an ultrathin heat-generating body can be produced at a high speed.

The invention claimed is:

1. A heat-generating body for warming a foot which comprises a container bag formed of a base material and a covering material and said container bag being charged with a formed heat-generating composition which can cause a heat generating reaction in the presence of air, the container bag being air permeable on at least at a part thereof; the formed heat-generating composition has a water mobility value of from 6 to 20, and the heat-generating composition contains, as essential components, from 1.0 to 50 parts by weight of a carbon component, from 0.1 to 10 parts by weight of a reaction accelerator and from 20 to 60 parts by weight of water, per 100 parts by weight of iron powder as a heat-generating substance generating heat upon reaction with oxygen, to which at least one kind selected from the group consisting of a water retaining agent, a water absorbing polymer, a pH adjusting agent, a hydrogen generation suppressing agent, a syneresis preventing stabilizer, a surface active agent, a defoaming agent, a hydrophobic polymer compound, a pyroelectric substance, a far infrared ray radiating substance, a negative ion generating substance, an aggregate, a fibrous material, a thickener, a binder, a fertilizer component and a heat-generating assistant is mixed depending on necessity.

2. A heat-generating body for warming a foot as described in claim 1, characterized in that the formed heat-generating composition has a structure containing two or more layers having different compositional ratios.

3. A heat-generating body for warming a foot as described in claim 1, characterized in that a part of at least one of the base material and the covering material has a water absorbing capability, water of the formed heat-generating composition is absorbed by a material having water absorption property among the base material and the covering material, and the heat generating body is substantially in a state capable of generating heat in air.

4. A heat-generating body for warming a foot as described in claim 1, characterized in that the container bag, constituting the heat-generating body for warming foot, is water non-absorbing, and the formed heat-generating composition is in a dehydrated state to enable substantial heat generation in air by at least one means selected from the group consisting of physical forced drainage by compression, decompression, compression and decompression; diffusion of water content by allowing to stand, and water absorption with a water absorbing material or a water absorbing agent.

5. A heat-generating body for warming a foot as described in claim 1, characterized in that concave and convex parts are provided on a part of at least one of the base material and the covering material, and a heat-generating composition is provided at least on the concave part.

6. A heat-generating body for warming a foot as described in claim 1, characterized in that concave and convex parts are provided on a part of at least one of the base material and the covering material.

7. A heat-generating body for warming a foot as described in claim 1, characterized in that an air permeable adhesive layer is provided between the heat-generating composition and a member selected from the group consisting of the base material and the covering material.

8. A heat-generating body for warming a foot as described in claim 1, characterized in that the base material and the covering material are sealed at least at an outer peripheral part of the formed heat-generating article by adhesion, cohesion or fusion.

9. A heat-generating body for warming a foot as described in claim 1, characterized in that the heat-generating body for warming a foot corresponds to a plane surface of an entire foot.

10. A heat-generating body for warming a foot as described in claim 1, characterized in that the heat-generating body for warming a foot corresponds to a plane surface of a part of a foot.

11. A heat-generating body for warming a foot as described in claim 1, characterized in that the heat-generating body for warming a foot has a part having no formed heat-generating composition present, and has at least one part, at which the heat-generating body is capable of being folded up at that part.

12. A heat-generating body for warming a foot as described in claim 1, characterized in that the container bag has an antislipping layer on at least a part thereof.

13. A heat-generating body for warming a foot as described in claim 1, characterized in that an adhesive agent layer is laminated on at least a part of at least one of exposed surfaces of at least one of the base material and the covering material.

14. A heat-generating body for warming a foot as described in claim 1, characterized in that a medical or sanitary agent is carried on at least one kind selected from the group consisting of a formed heat-generating composition, an adhesive agent layer, the base material and the covering material.

15. A heat-generating body for warming a foot as described in claim 1, characterized in that at least one of a character, a symbol, a numeral, a pattern, a photograph and a picture is provided on at least a part of constitutional components of the heat-generating body for warming a foot.

16. A heat-generating body for warming a foot as described in claim 1, characterized in that at least a part of constitutional components of the heat-generating body for warming a foot is colored.

17. A heat-generating body for warming a foot as described in claim 1, characterized in that the heat-generating body for warming a foot is charged and sealed in an air nonpermeable container bag.

18. A process for producing a heat-generating body for warming a foot characterized in that the production process contains steps of laminating a heat-generating composition as described in claim 1 as a formed heat-generating composition laminated in a form covering an arbitrary part of a foot on at least one prescribed region on a base material in a film form or a sheet form, and overlaying a covering material, and the production process contains a step 1, a step 2 and a step 4 sequentially carried out as a basic process, and depending on necessity, with a step selected from the step 1, the step 2, a step 2A, a step 2B, a step 3, a step 3A, a step 3B, a step 3C, the step 4, a step 5, a step 6, a step 7 and a step 8 with possible duplications being subjected to arbitrary inter position in the basic process wherein the steps being the following:

Step 1: a step of producing the heat-generating composition;
Step 2: a step of forming;
Step 2A: a forming step using a leveling plate and a magnet;
Step 2B: a forming step using a pressing plate equipped with a vibrating device;
Step 3: a laminating, diffusing or coating step on the heat-generating composition;
Step 3A: a step of providing an air permeable adhesive polymer;
Step 3B: a laminating, diffusing or coating step on the base material;

Step 3C: a step of subjecting the heat-generating composition to a surface treatment;

Step 4: a step of covering;

Step 4A: a step of laminating by a means selected from the group consisting of heat fusion, press adhesion, and heat press adhesion;

Step 5: a step of compressing;

Step 6: a step of dehydrating;

Step 7: a step of punching; and

Step 8: a step of charging the heat-generating body in an air nonpermeable container bag.

* * * * *